(12) United States Patent
Yasuda et al.

(10) Patent No.: US 6,361,953 B1
(45) Date of Patent: Mar. 26, 2002

(54) CELL COMPONENT RECOVERY METHOD

(75) Inventors: Kenji Yasuda, Hiki-gun; Kazunori Okano, Shiki; Hirokazu Kato, Hiki-gun, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/666,883

(22) Filed: Sep. 20, 2000

Related U.S. Application Data

(63) Continuation of application No. 09/552,465, filed on Mar. 9, 2000, now Pat. No. 6,218,126, which is a continuation of application No. 09/329,318, filed on Jun. 10, 1999, now Pat. No. 6,093,370.

(30) Foreign Application Priority Data

| Jun. 11, 1998 | (JP) | 10-163213 |
| Nov. 20, 1998 | (JP) | 10-330536 |
| Dec. 22, 1998 | (JP) | 10-364059 |
| Jan. 27, 1999 | (JP) | 11-018004 |

(51) Int. Cl.$^7$ ............ C12Q 1/68; C12M 1/34; G01N 15/06; B01L 11/00
(52) U.S. Cl. ........ 435/6; 435/287.2; 435/288.2; 435/288.4; 435/2; 422/50; 422/68.1; 422/101
(58) Field of Search ............ 435/2, 6, 287.2, 435/288.2, 288.4; 422/50, 101, 68.1

(56) References Cited

U.S. PATENT DOCUMENTS

| 4,446,237 A | 5/1984 | Berninger ............ 436/804 |
| 4,893,886 A | 1/1990 | Ashkin et al. ........ 350/1.1 |
| 5,605,662 A | 2/1997 | Heller et al. ........ 422/68.1 |
| 5,607,646 A | 3/1997 | Okano et al. ........ 422/101 |
| 5,800,992 A | 9/1998 | Fodor et al. ........ 435/6 |
| 6,060,288 A | 5/2000 | Adams et al. ........ 435/91.2 |
| 2001/0000149 A1 * | 4/2001 | Smith et al. ........ 435/6 |

FOREIGN PATENT DOCUMENTS

GB WO-98/51693 A1 * 11/1998

OTHER PUBLICATIONS

"Space–Resolve Control of Protein Suburst Dissociation/Association Using Laser Heating", 94 Aug. 1994, M. Washizu et al. pp. 111–114.
"Scanning Tunnelling Microscopy of Mercapto–Hexyl–Oligonucleotides Attached to Gold", BIOPHYSICAL JOURNAL, vol. 71, Aug. 1996, D. Rekash et al. pp. 1079–1086.
"Electrostatic Manipulation of Bioparticles", KONA. No. 14, M. Washizu, pp. 61–71. (No Year Presented).
"Light–Directed, Spatially Addressable Parallel Chemical Synthesis", SCIENCE, vol. 251, Feb. 15, 1991, Fodor et al. pp. 767–773.
"Remote Thermal Imaging With 0.7 –um Spatial Resolution Using Temperature–Dependent Fluorescent Thin Films", APPLIED PHYSICAL LETTERS. 42(1).
"Covalent Attachment of hyoridizaole Oligonucleotides to Glass Supports", ANALYTICAL BIOCHEMISTRY, vol. 247, 1997, 1997, B. Joos et al. pp. 96–101.
Covalent Immobilization of DNA onto Polystyrene Microworks: The Molecules Are Only Bound at the 5 "End", ANALYTICAL CHEMISTRY, 198, 1991. S. Raamussen et al. pp. 138–142.
"DNA Analysis and Diagnosis on Oligonecleotides Microchips", PROCEEDINGS NATIONAL ACADEMY OF SCIENCE USA, 93, 1996, G. Yershov et al.

* cited by examiner

Primary Examiner—W. Gary Jones
Assistant Examiner—B J Forman
(74) Attorney, Agent, or Firm—Mattingly, Stanger & Malur, P.C.

(57) ABSTRACT

Different probes each having a specific base sequence are immobilized to each of independent areas formed on the surface of a substrate, complementary polynucleotides in a sample solution are hybridized to the probes, and each of the independent areas on the substrate is heated and then cooled in sequence, and hence the solution is recovered to extract different polynucleotides separately corresponding to individual probes.

9 Claims, 25 Drawing Sheets

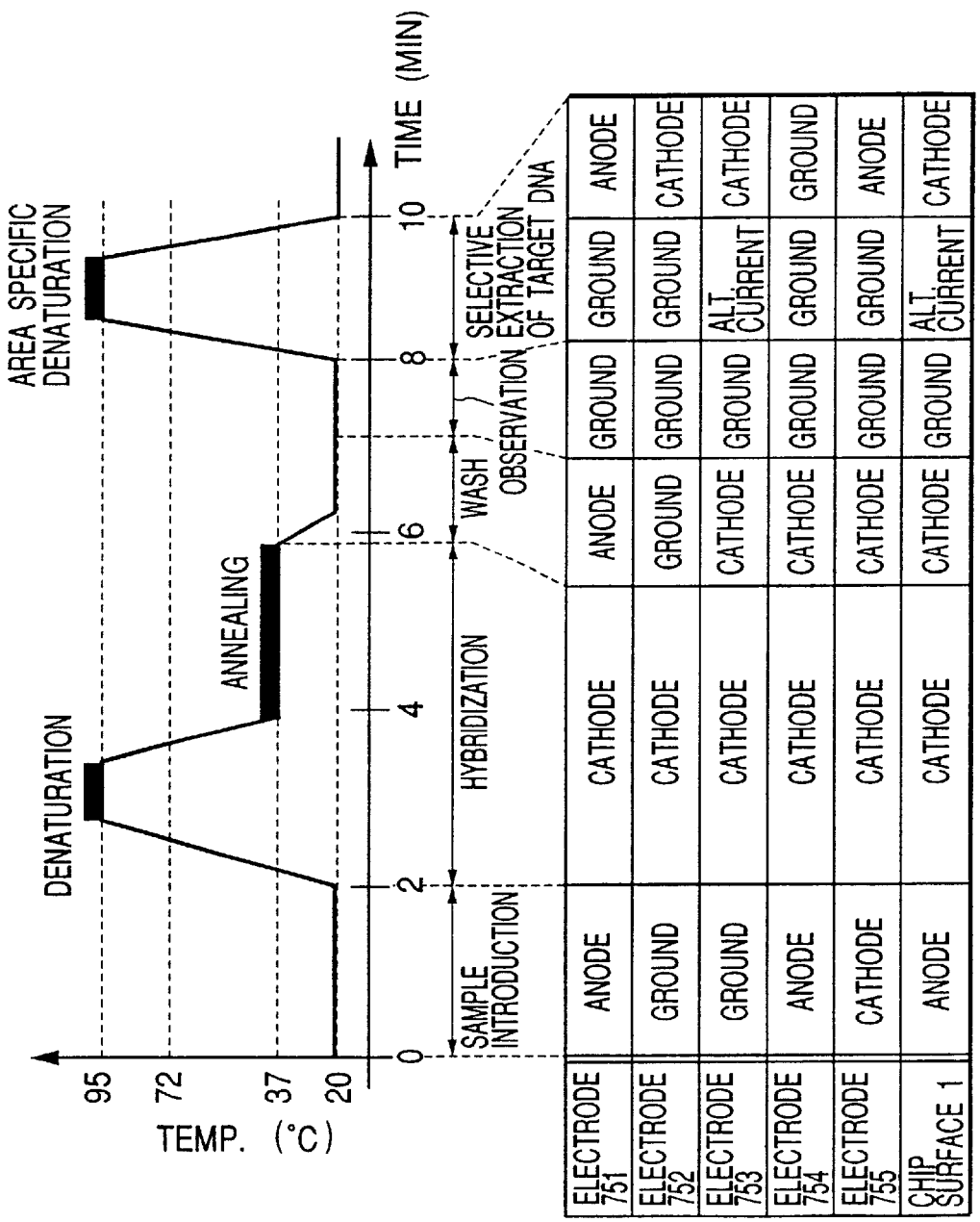

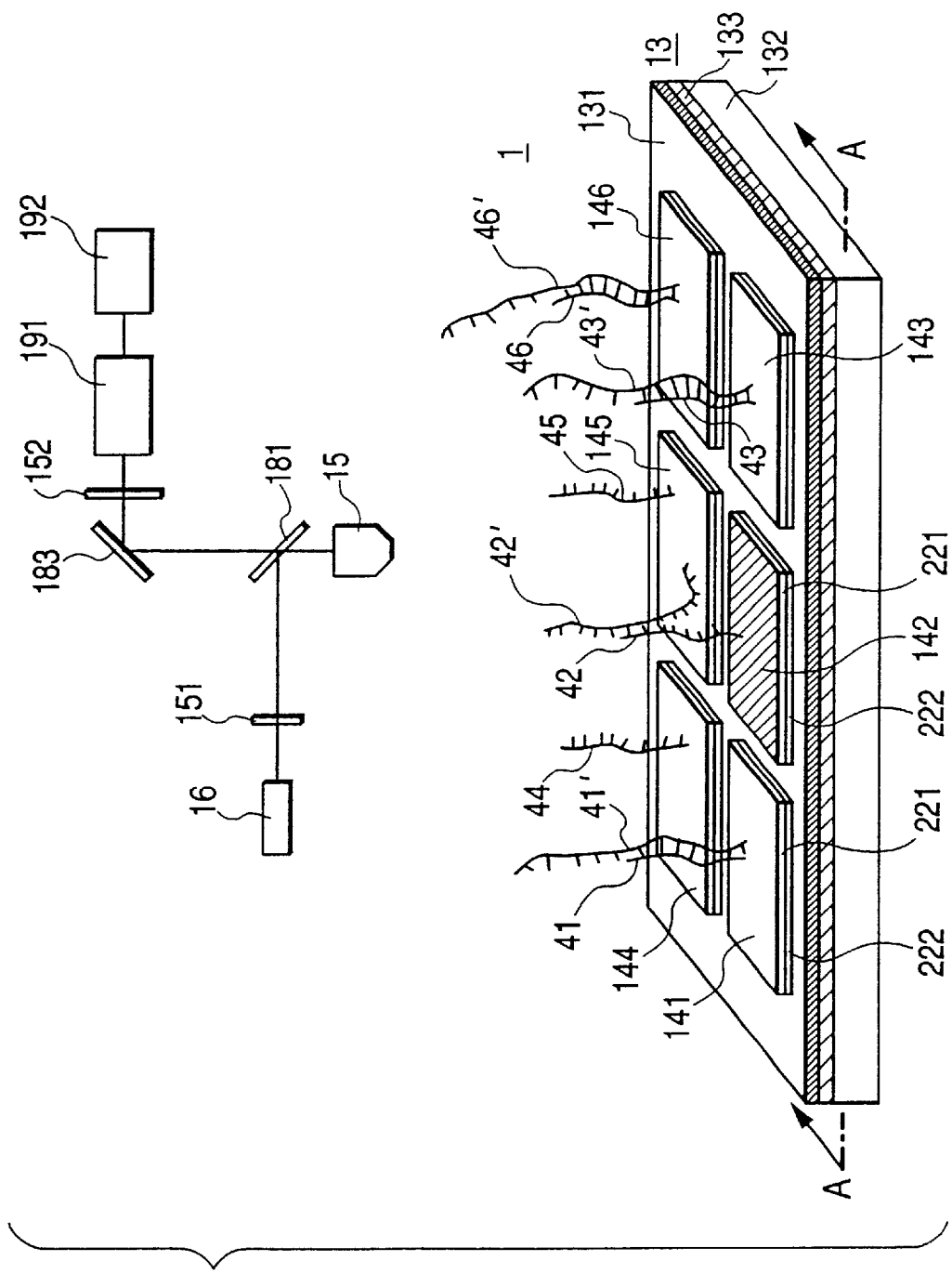

CELL COMPONENT RECOVERY METHOD

This application is a continuation of U.S. application Ser. No. 09/552,465, filed Mar. 9, 2000 now U.S. Pat. No. 6,218,126 which is a continuation of U.S. application Ser. No. 09/329,318, filed Jun. 10, 1999 now U.S. Pat. No. 6,093,370.

BACKGROUND OF THE INVENTION

The present invention relates to a method for selectively extracting a target polynucleotide having a specific base sequence from a polynucleotide mixture sample having a plurality of different sequences or from cells, and an apparatus therefor.

A DNA chip is one of means for detecting a specific base sequence of DNA quickly and easily. It utilizes micropatterning techniques used in microprocessing of semiconductors and the complementarity of DNA. In this technique, DNA sequence of a sample solution is analyzed in the following manner: Single stranded-oligonucleotides as probes having different sequences each of a length of approximately 8–9 bp are immobilized separately onto each of two-dimensionally split individual areas on a substrate; the sample solution containing DNA is added dropwise to the substrate to hybridize the DNA separately with each of probes in each of the areas of the substrate while attaching a fluorescent dye to the hybrids simultaneously in the hybridization step; and the magnitude of the hybridization between the probes and DNA in the sample solution is optically determined through emitted fluorescence to analyze the DNA sequence in the sample solution.

U.S. Pat. No. 4,446,237 discloses a method for capturing a target oligonucleotide (DNA or RNA) as a probe on a solid phase. According to this method, the oligonucleotide in a sample solution is denatured into single strands by heating, which is then immobilized on the surface of a nitrocellulose membrane. S. R. Rasmussen et al. describe another method for capturing a target oligonucleotide sample on a solid phase in Analytical Biochemistry 198, 128–142 (1991). According to the method, the phosphate group at the 5'-end is activated by using 1-methylimidazole and 1-ethyl-3-(3-dimethylaminopropyl)carbodiimide. The activated polynucleotide is then immobilized onto a polystyrene microplate having a secondary amine on its surface. The activated 5'-end phosphate group reacts with the secondary amine, so that the 5'-end of the polynucleotide is covalently immobilized onto the microplate surface.

As thus described, a target polynucleotide in a sample solution can be captured and analyzed by selectively hybridizing a target polynucleotide (DNA or RNA) with a complementary oligonucleotide immobilized as a probe on a membrane surface. The DNA chip is on the basis of this concept.

Okano et al. describe a method for extracting target polynucleotides by hybridizing the target polynucleotides to probes immobilized on a chip, heating the chip to denature the captured polynucleotides on the probes to separate and collect them from the chip in U.S. Pat. No. 5,607,646.

A method for selectively extracting a target polynucleotide by utilizing difference in rates in electrophoresis of polynucleotides in gel has been in wide use.

SUMMARY OF THE INVENTION

The gene analysis technology using a DNA chip described in the above is a technique for hybridizing and analyzing a target polynucleotide (DNA or RNA) by complementarily hybridizing single-stranded polynucleotides derived from the target polynucleotide in a sample solution with a probe (a specific single stranded-oligonucleotide) with a length of 8–9 bp formed on a substrate. This technique is never directed to further extract the captured or hybridized DNA or RNA single stranded-polynucleotide on the probe from the substrate selectively.

Conventional techniques give no consideration of extracting a target polynucleotide to be extracted directly from cells.

According to conventional separating techniques using electrophoresis, the mobility of each of polynucleotides is relative to each other and fluctuates with changes of electrophoresis conditions, and thus identification of an extracted sample solution component is required. In addition, exact separation and purification of a trace quantity of a target polynucleotide is difficult because diffusion in the electrophoresis step can invite contamination of polynucleotides with each other.

It is, therefore, an object of the present invention to provide a process and apparatus for selectively extracting a trace quantity of a target polynucleotide (DNA or RNA) having a specific base sequence rapidly with a high precision.

The invention proposes, to achieve the above object, selective extraction of a target polynucleotide alone from a sample solution by modifying each of independent split areas on the surface of a substrate separately with each of probes (specific oligonucleotides) having different base sequences respectively, hybridizing polynucleotides (DNA or RNA) in the sample solution separately to the probes, and then heating a specific area alone of the substrate selectively to allow a polynucleotide alone complementarily hybridized with the heated probe to liberate from the probe.

BRIEF DESCRIPTION OF THE DRAWINGS

These and other features, objects, and advantages of the present invention will become apparent upon a consideration of the following description of the invention when read in conjunction with the drawings, in which:

FIGS. 9A, 9B and 9C are timetables respectively illustrating the nucleotide separation process according to the first embodiment of the invention;

FIG. 10 is a diagram illustrating the relationship between a substrate 1 having a target polynucleotide hybridization area and an optical system for detecting the hybridization in the target polynucleotide hybridization area, according to a second embodiment of the invention;

DESCRIPTION OF THE PREFERRED EMBODIMENT

Figure 1:
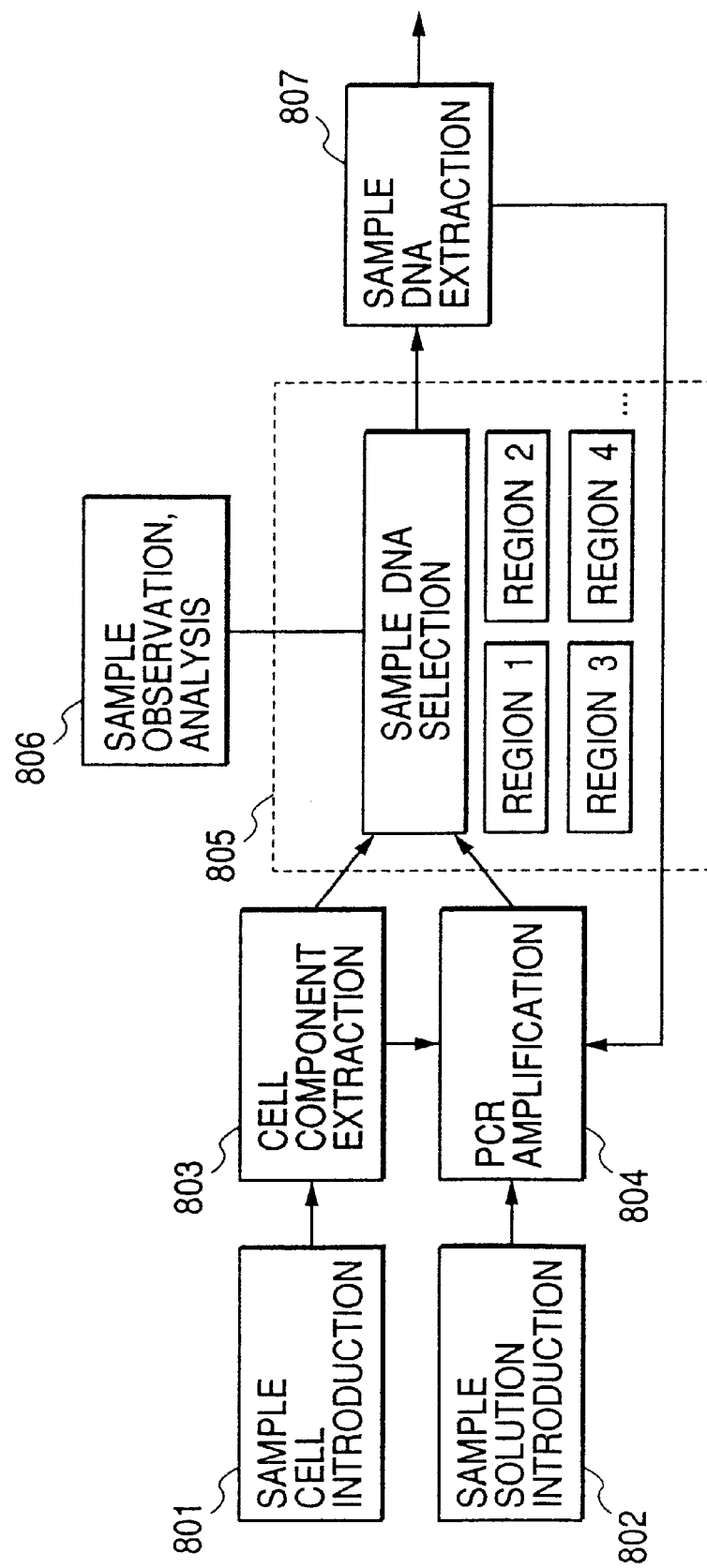
FIG. 1 is a gene processing flowchart for demonstrating where the method and apparatus for separating polynucleotides according to the invention are located in analysis and selective extraction process of gene.

FIG. 1 is a gene processing flowchart for demonstrating where the method and apparatus for separating polynucleotides according to the invention are located in analysis and selective extraction process of gene. Processes 801 and 802 are preparative processes respectively for sample cell introduction and sample solution introduction, respectively. The present invention can be applied both to cells and solutions as samples. Process 803 is a cell component extraction process. Process 804 is a PCR amplification process, being conducted when a target polynucleotide has a low concentration. Process 805 is a process for sample DNA selection on a plurality of independent areas, which characterizes the invention. Process 806 is a selected sample observation analysis process. Process 807 is sample DNA extraction process from the independent areas.

According to the invention which includes a process for sample DNA selection on a plurality of independent areas and wherein each DNA is extracted from each of the areas, efficient fractionation can be achieved, as described in detail hereinbelow.

EMBODIMENT I

Figure 2:
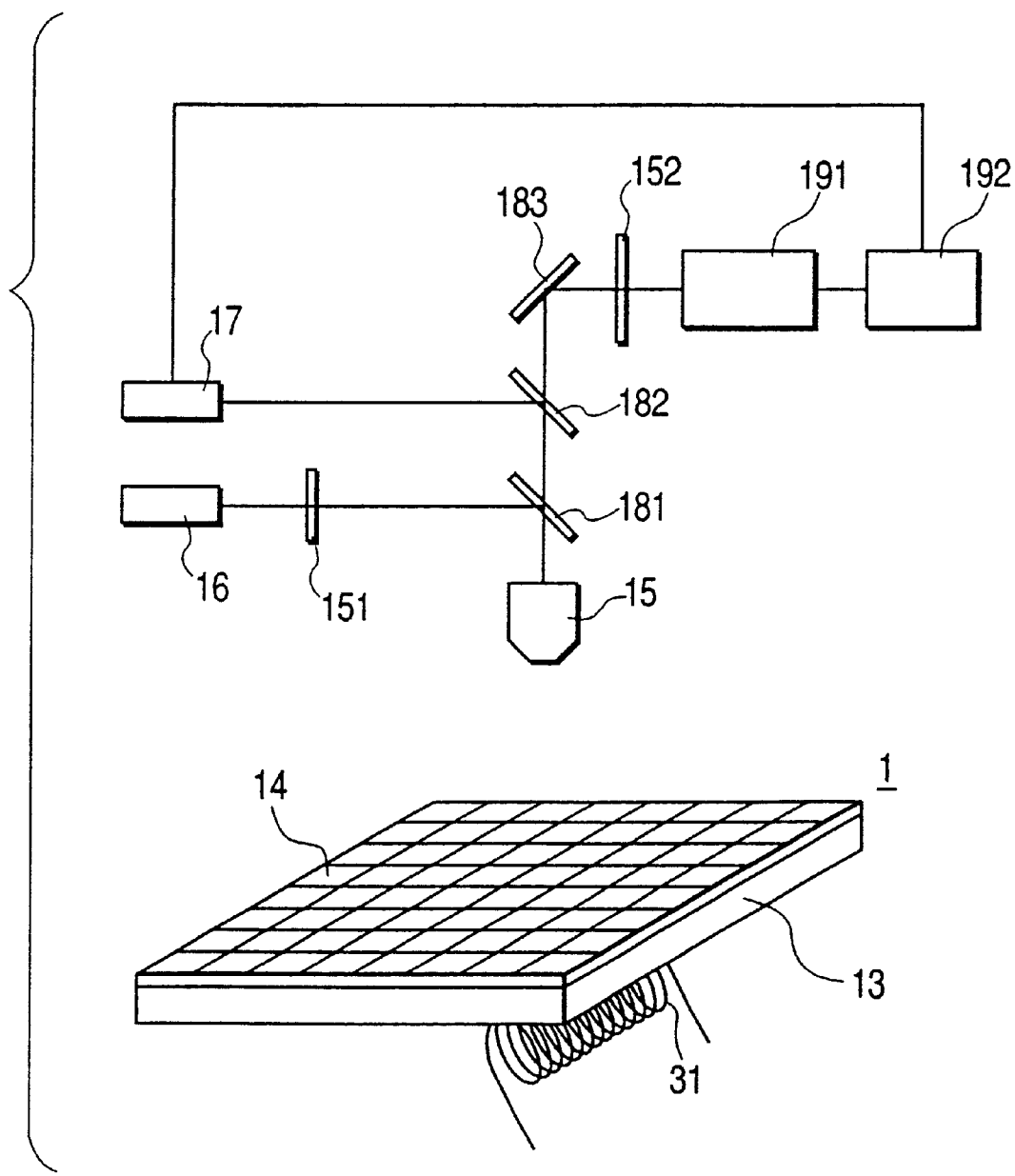
FIG. 2 is a schematic diagram illustrating a basic configuration according to a first embodiment of the invention.

FIG. 2 is a schematic diagram illustrating a basic configuration of a first embodiment of the invention. Substrate 1 is for hybridizing and selecting a target polynucleotide to be extracted on its surface, comprising substrate base 13 and target polynucleotide hybridization areas 14 which are two-dimensionally mounted on the surface of the substrate base 13 by splitting to the order of 1 micrometer square by means of a light exposing technique. A plurality of probes (single stranded-oligonucleotides) having a different sequence for each area with a length of about 8–9 bp are individually immobilized on the surface of each of the target polynucleotide hybridization areas 14. The probes are oligonucleotides complementary to a target polynucleotide in a sample solution. When the sample solution reaches the surfaces of the target polynucleotide hybridization areas 14, the probes hybridize with the target polynucleotide. In other words, the target polynucleotide is captured by the probes. Upon the hybridization between the probes and the target polynucleotide, a fluorescent dye simultaneously attaches to the hybrids. Heater 31 is provided on the back of the substrate 1 and capable of heating the whole surface of the substrate 1 from around room temperature up to about 95° C. The substrate 1 is disposed in the direction perpendicular to the optical axis of object lens 15. Each of light source 16 for fluorescence observation and infrared laser source 17 for convergent light beam irradiation is disposed in the direction perpendicular to the optical axis of the object lens 15. Dichroic mirrors 181, 182 are disposed at the positions where the optical axis of the object lens 15 intercepts with the optical axes of the light sources 16 and 17 respectively, to induce lights irradiated from the light sources 16 and 17 respectively to the objective lens 15. The light from the light source 16, the fluorescence from the florescent dye and the light from the light source 17 may preferably have a different wavelength from each other. The light from the light source 16 can be converged through bandpass filter 151 to adequate wavelengths for exciting the fluorescent dye. The exciting light induced to the objective lens 15 is converged to excite the fluorescent dye attached to the target polynucleotide hybridized and selected on the substrate. The excited fluorescent dye emits fluorescence in an intensity proportional to each amount of the target polynucleotide hybridized to probes of each of the individual areas of the substrate. Mirror 183 is to reflect a light beam which is obtained by collecting the emitted fluorescence through the objective lens 15. Emission filter 152 is to selectively transmit only a light beam having a wavelength range of fluorescence to be detected. Detector 191 is to detect the intensity of the fluorescence transmitted through the emission filter 152.

The spatial distribution of the amount of the target polynucleotide in the sample solution which has been hybridized to the probe immobilized on the substrate can be obtained as a fluorescence image by moving mutually the objective lens 15 and the substrate 1 and scanning the surface of the substrate 1 in sequence with the exciting light induced through the objective lens 15 to find the spatial distribution of the fluorescence emission intensity emitted by the fluorescent dye. When the fluorescent dye attached with the target polynucleotide is excited for observation, the use of an exciting light having a wavelength in the visible region and a fluorescent dye capable of fluorescing by means of a visible light are preferred in the observation of the fluorescence from the dye attached with the target polynucleotide. An autoemission fluorescence of the target polynucleotide can also be observed instead of light emission of the fluorescent dye attached to the target polynucleotide. In this case the exciting light preferably has a wavelength of near UV region ranging from 280 nm to 400 nm.

The fluorescence emission intensity of the fluorescent dye decreases in proportion to an increasing temperature through the function of the thermal quenching effect. By using this phenomena, an area specific temperature increase in the target polynucleotide hybridization areas on the substrate can be determined according to the present embodiment. According to the apparatus illustrated in FIG. 2, changes of the fluorescence emission intensity of the fluorescent dye attached with the target polynucleotide, which has been detected by the detector 191 can be analyzed with analyzer 192 based upon the temperature-dependency of changes of the fluorescence emission intensity, and the temperature of the target polynucleotide hybridization areas can thus be estimated.

An infrared light emitted by the infrared laser source 17 is reflected on the dichroic mirror 182 downward, converged on the objective lens 15 and irradiated to a target polynucleotide hybridization area 14 formed on the substrate 1. In the target polynucleotide hybridization area 14, a thin film layer or particle layer formed on the substrate 1 absorbs infrared light to evolve heat and thereby to area-specifically increase the temperature in the sample solution. The convergent position of the light from the laser source 17 converged on the objective lens 15 on the surface of the substrate 1 can be changed arbitrarily by moving the objective lens 15 or moving the substrate 1. To avoid damage to the hybridized target polynucleotide, the use of a light having a wavelength region not to be absorbed by the target polynucleotides is preferred. By way of illustration, near infrared light having a wavelength of equal to or more than 800 nm or visible light having a wavelength of equal to or more than 400 nm is preferably used.

It is known that a single stranded-polynucleotide such as DNA or RNA, being complementary to another single stranded-polynucleotide such as a probe, forms base pairs through hydrogen bonds with the complementary polynucleotide to form a double stranded-polynucleotide; and that the double stranded-polynucleotide formed by base pairs through hydrogen bonds denatures to form single stranded-polynucleotides when the temperature of a sample solution is increased up to about 95° C. Accordingly, by irradiating the convergent infrared ray to a specific target polynucleotide hybridization area 14 on the substrate to increase its temperature up to 95° C., the target polynucleotide hybridized to the probe on the specific target polynucleotide hybridization area can selectively separated.

The probes on the substrate 1 and polynucleotides in the sample solution above the substrate 1 can be elongated when a planer electrode is placed on the substrate 1 and an alternating field is applied between the planer electrode and the substrate 1. Consequently, nonspecific hybridization between the probes and polynucleotides in the sample solution can be reduced and denaturation of the pairs between the probes and the target polynucleotide through the convergent light can efficiently be achieved.

The denaturing temperature of the target polynucleotides hybridized to the probes increases in proportion to the amount of hydrogen bonds therebetween, and polynucleotides can selectively be fractionated in accordance with the magnitude of hybridization matching between the target polynucleotides and the probes by controlling the denaturing temperature. In other words, the target polynucleotides hybridized to the probes begin to denature with an gradually increasing temperature, whereas the less the polynucleotides have hydrogen bonds, the earlier they begin to denature. The target polynucleotides can, therefore, be selectively fractionated in consideration with the magnitude of specific bonds by feedback-controlling the output of the laser source 17 based upon the temperature information obtained through the analyzer 192 and adjusting the temperature of the target polynucleotide hybridization areas 14.

The variations of the denaturing temperatures of target polynucleotides hybridized to probes can be minimized by adding a tertiary ammonium salt such as tetramethylammonium chloride to the sample solution.

Figure 3:
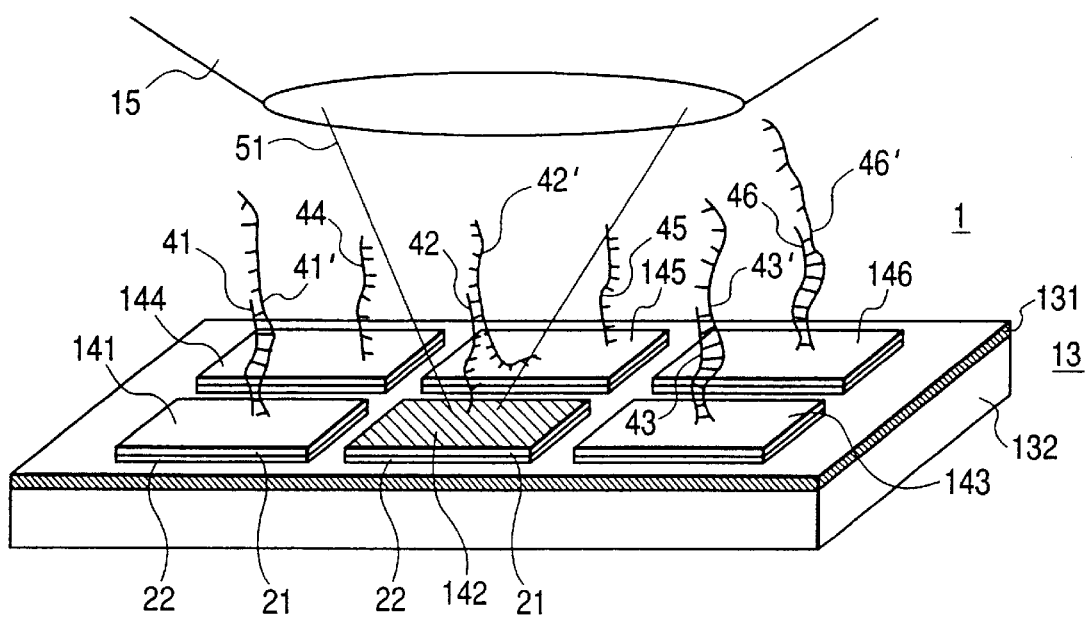
FIG. 3 is a schematic diagram illustrating a first means for heating a specific area on a substrate of the first embodiment.

FIG. 3 illustrates a first means for heating a specific area of the target polynucleotide hybridization areas 14 on the substrate. According to the present embodiment, substrate base 13 is composed of electrically conductive film 131 provided on the surface side and thermally conductive insulating substrate 132. Onto the electrically conductive film 131 are placed a plurality of target polynucleotide hybridization areas 141, 142, 143, 144, 145 and 146. Each of the target polynucleotide hybridization areas has a dual-layer structure composed of photoabsorbing layer 21 such as an aluminium oxide thin film and heat-insulating layer 22. Probes (oligonucleotides) 41, 42, 43, 44, 45 and 46 each having a length of 8–9 bp are respectively immobilized to the surface of each of the target polynucleotide hybridization areas separately. FIG. 3 schematically illustrates the state where target polynucleotides 41', 42', 43' and 46' are respectively hybridized only to the probes 41, 42, 43 and 46 of these probes. By identifying the target polynucleotide hybridization areas through fluorescence observation, the complementarity of the target polynucleotides hybridized to the probes among polynucleotides in the sample solution can be estimated. In the embodiment illustrated in the figure, the probes in the areas 141, 142, 143 and 146 complementarily hybridize to the target polynucleotides, whereas those in the areas 144 and 145 do not, indicating that there is no polynucleotide having complementary relation with the probes in the areas 144 and 145.

Convergent light 51 is then irradiated through the objective lens 15 to the target polynucleotide hybridization area 142 where the target polynucleotide 42' is hybridized to the probe 42; the photoabsorbing layer 21 in the area 142 absorbs the convergent light 51 and evolves heat. The heat from the photoabsorbing layer 21 in the area 142 allows the vicinity of the area 142 to increase its temperature up to about 95° C., and hence hydrogen bonds between the probe 42 and the target polynucleotide 42' are dissociated to denature the target polynucleotide 42' alone which has been hybridized to the area 142. When the size of an area where the convergent light is converged is smaller than that of a unit target polynucleotide hybridization area, the light axis should be adjusted to ensure that the convergent area is within the target polynucleotide hybridization area. When a unit target polynucleotide hybridization area has a smaller size than the convergent area of the convergent light, individual areas should preferably be arranged in such a manner that gaps between individual target polynucleotide hybridization areas are sufficient and only one area is to be heated by the convergent light. In FIG. 3, only one probe is shown in each target polynucleotide hybridization area to be easy to read, but in practice, a plurality of probes having an identical base sequence are generally immobilized to each area.

According to the present embodiment, where the electrically conductive film 131 is placed on the surface of the substrate base 13, probes and/or polynucleotides can be elongated by providing a counter electrode plate (not shown) above the substrate 1 and applying an alternating field between the electrode plate and the substrate, as described above. By this configuration, erroneous hybridization in the hybridization step and steric entanglement in the denaturation of the target polynucleotide from the probe by heating the target polynucleotide hybridization area can be prevented to ensure an efficient processing.

In addition, the cooling effect through the absence of the convergent light 51 irradiation can be improved by using the thermally conductive insulating substrate 132 as the substrate base 13.

The photoabsorbing layer 21 according to the present embodiment may be prepared by vapor deposition, as well as by coating or spraying. The target polynucleotide hybridization areas can be formed in the shape of square or rectangular, as well as round or ellipse in accordance with the shape of the convergent light.

Figure 4:
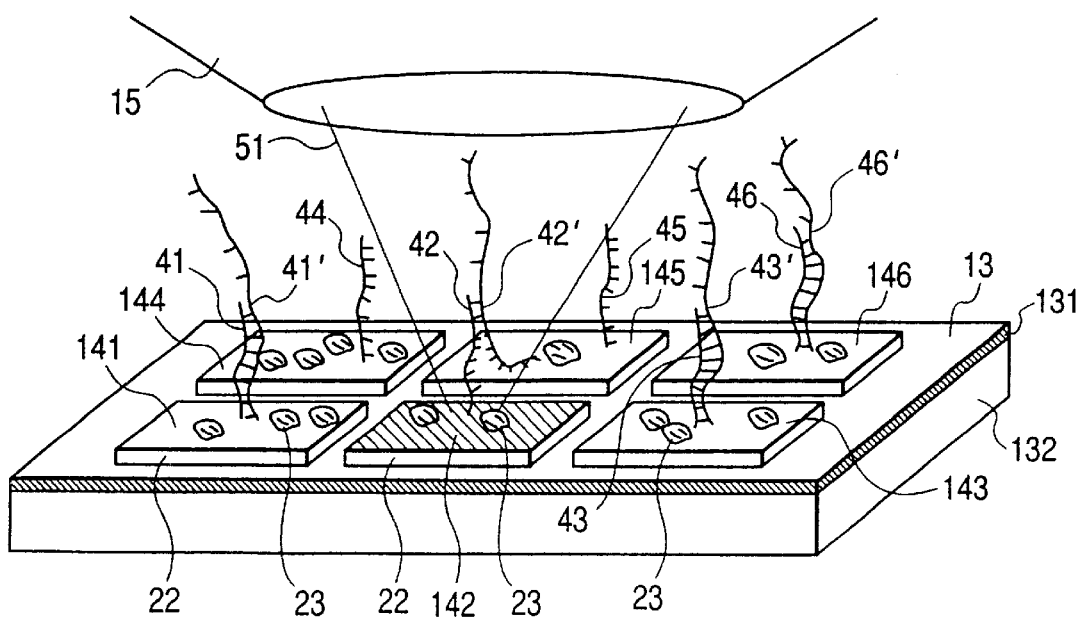
FIG. 4 is a schematic diagram illustrating a second means for heating a specific area on the substrate according to the first embodiment.

FIG. 4 illustrates a second means for heating a specific area on the substrate 1. The photoabsorvable thin layer 21 is formed on the target polynucleotide hybridization areas in the embodiment of FIG. 3, whereas, in the present embodiment, particles 23 each having photoabsorbing characteristics and have sufficiently small sizes in comparison with those of the target polynucleotide hybridization areas are dispersed and placed on the target polynucleotide hybridization areas. At least one particle should be placed on each area. According to the present embodiment, heat insulating layer 22 is separately provided in each of individual areas and the particles 23 are placed onto the upper surface of the insulating layer 22. The substrate 1 comprises substrate base 13 composed of electrically conductive film 131 and thermally conductive insulating substrate 132 as well as in the embodiment illustrated in FIG. 3.

When the convergent light 51 is irradiated to a specific target polynucleotide hybridization area 142, the particle 23 in the area absorbs the light to evolve heat and hence the vicinity of the area 142 alone is increased in temperature so that the target polynucleotide alone being hybridized to the probe on the area 142 can be denatured from the probe. According to the present embodiment, the use of particles 23 ensures an area, smaller than the convergent range of the convergent light of the present embodiment of FIG. 3, to be heated specifically, whereas the size of each target polynucleotide hybridization area and that of the convergent area of the convergent light have a similar relation as in the embodiment of FIG. 3. The photoabsorbing layer composed of the particles 23 according to the present embodiment can be-prepared by coating or spraying of particles. The particles can be shaped arbitrarily as in the embodiment of FIG. 3.

Figure 5:
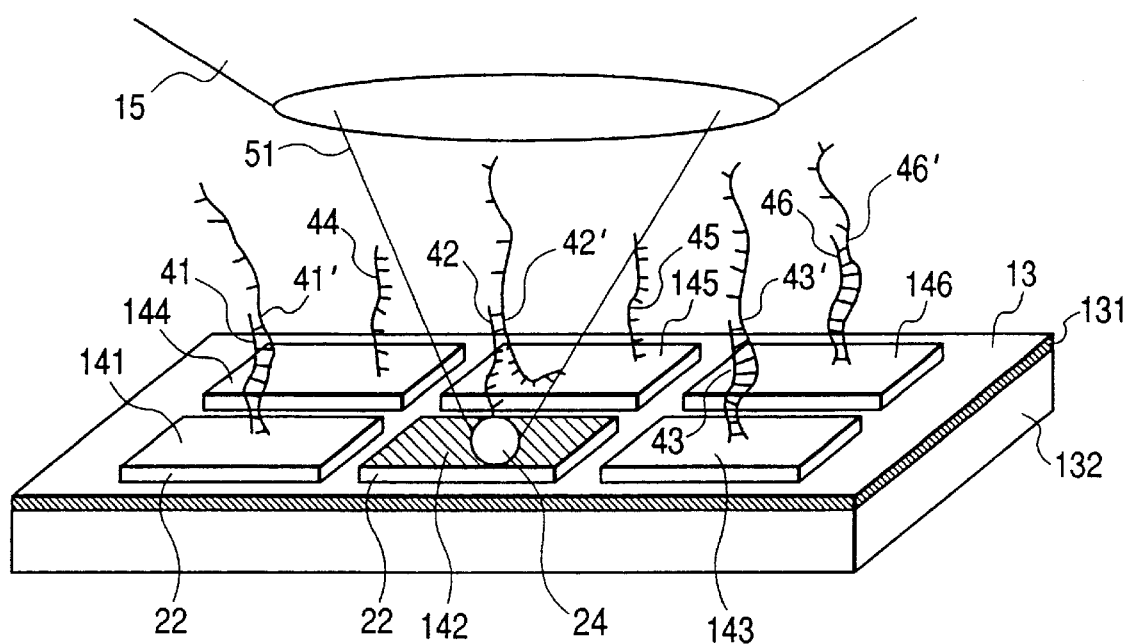
FIG. 5 is a schematic diagram illustrating a third means for heating a specific area on the substrate according to the first embodiment.

FIG. 5 illustrates a third means for heating a specific area on the substrate 1. The present embodiment is similar to the embodiment of FIG. 4 in that temperature increase by particle 24, which absorbs light at wavelength region of the convergent light, is utilized, but different from the latter in that the particle 24 is captured by the convergent light 51 in the manner of optical forceps, and the captured particle 24 is placed in a target polynucleotide hybridization area on which probe and the target polynucleotide are to be denatured. The numerical aperture of the objective lens 15 in this case should preferably be equal to or more than 1.2 for ensuring satisfactory characteristics as optical forceps. Heat insulating layer 22 is also provided respectively in each area in the present embodiment. Substrate 1 comprises substrate base 13 composed of electrically conductive film 131 and thermally conductive insulating substrate 132 as well as in the embodiment of FIG. 3. As the embodiment of FIG. 5 is similar to the embodiment of FIG. 4 except that the particle 24 is captured in the manner of optical forceps, other descriptions concerning the figure are omitted.

According to the present embodiment, temperature increase by the particle 24 is confined within the vicinity of the particle 24 in the area where the particle 24 is placed, the sizes of the target polynucleotide hybridization areas and that of the convergent area of the convergent light have no fundamental relationship. To be more specific, temperature increase by the particle 24 is limited to the vicinity of the particle 24 in the area where the particle 24 is placed, and hence a target polynucleotide to be denatured is limited to that present in the target polynucleotide hybridization area where the particle 24 is place, even when the convergent area of the convergent light covers a plurality of target polynucleotide hybridization areas. The present embodiment is, therefore, advantageous in that the target polynucleotide hybridization areas can be arranged with an increased density.

Figure 6:
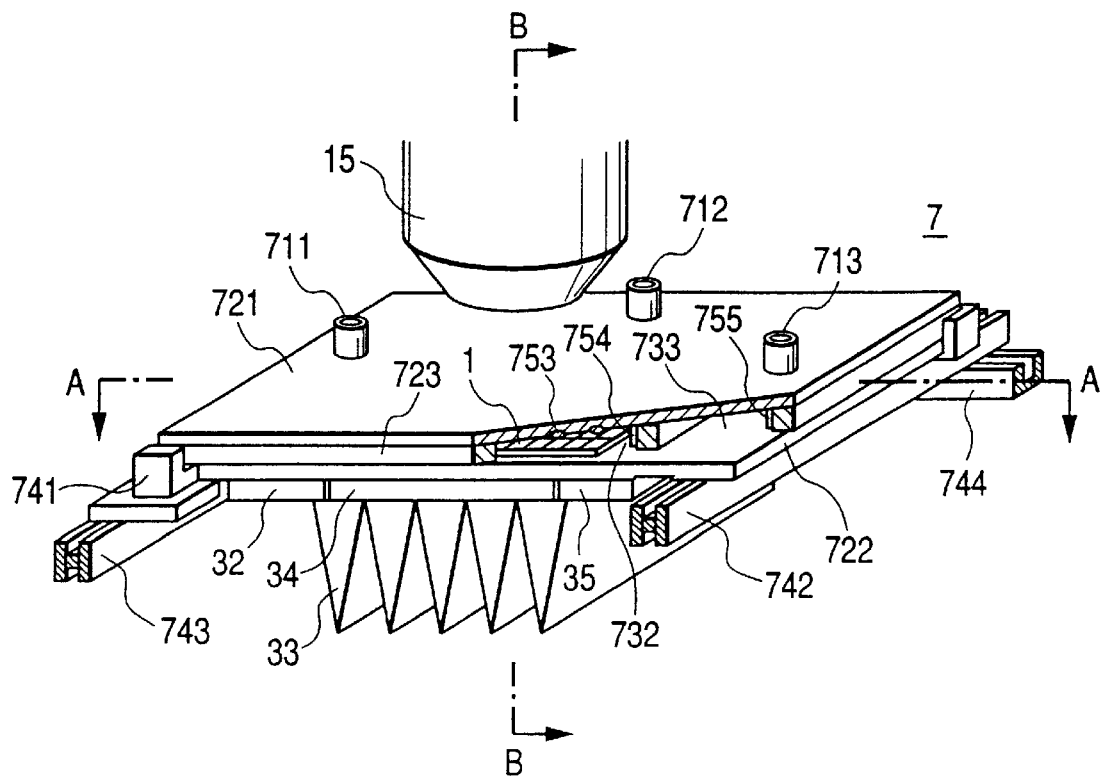
FIG. 6 is a schematic diagram illustrating a practical configuration of a polynucleotide separation cell according to the first embodiment.

FIG. 6 demonstrates a more detailed illustrative configuration including the relationship between the nucleotide separation cell 7 and the substrate 1 using the basic configuration of the embodiment shown in FIG. 2.

Figure 7:
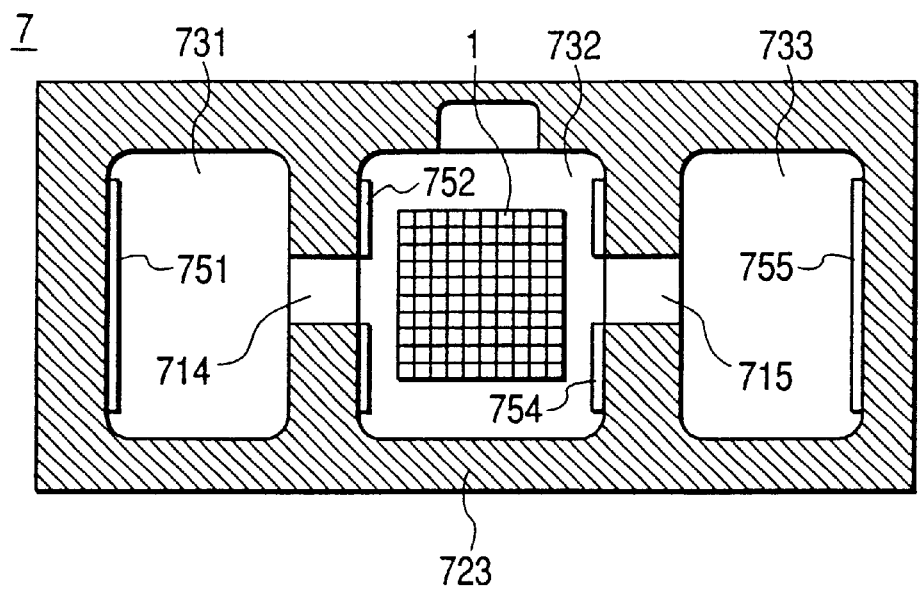
FIG. 7 is a sectional view along with the lines A—A of the cell illustrated in FIG. 6.
Figure 8:
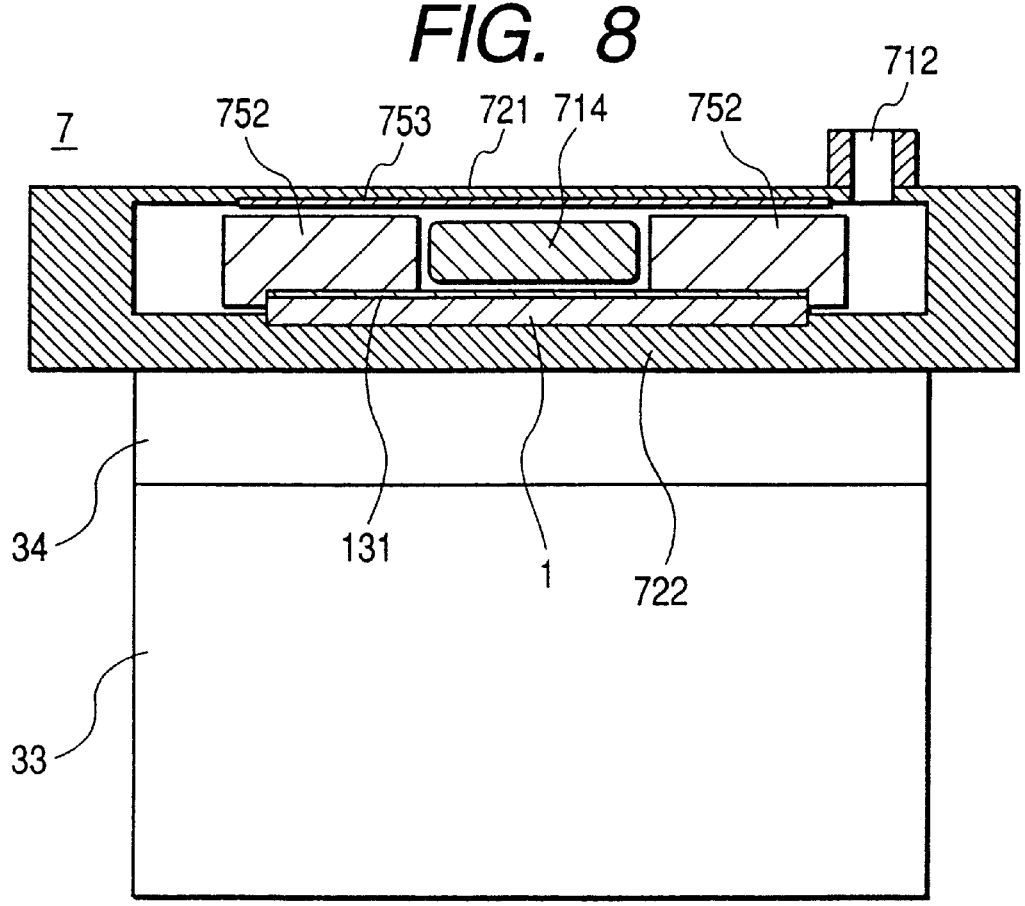
FIG. 8 is a sectional view along with the lines B—B of the cell illustrated in FIG. 6.

Part of the polynucleotide separation cell 7 in FIG. 6 is notched for viewing the inside thereof. FIGS. 7 and 8 are sectional views of the polynucleotide separation cell 7 respectively along with the lines A—A and the lines B—B.

The polynucleotide separation cell 7 is provided with upper cell plate 721, lower cell plate 722, and three sample solution chambers 731, 732 and 733 which are partitioned by a plurality of spacers 723. The upper cell plate 721 is fabricated of a light transmittable material. The tree sample solution chambers can import and export a sample solution through sample solution inlets 711, 712 and 713 respectively. Between each of the sample solution chambers are connected communication holes 714 and 715, through which the sample solution is transferred. The substrate 1 on which probes are immobilized as illustrated in FIG. 2 is mounted on the lower cell plate 722 in the sample solution chamber 732, and on the substrate 1 is integrated electrode plate 131 for applying an electric field. Electrodes 751, 752, 754 and 755 are attached to individual side walls of the sample solution chambers 731, 732 and 733 respectively, and mesh electrode 753 is placed on the inner wall of the upper cell plate for applying an electric field onto above the sample solution chamber 732. The temperature of the substrate 1 can be controlled within the range from 0° C. to 95° C. through Peltier devices 32, 34 and 35 each provided with a cooling plate 33, and individual temperatures of the sample solution chambers 731, 732 and 733 can be independently controlled within the range from 0° C. to 95° C. by operating the Peltier devices 32, 34 and 35 independently. Accordingly, the PCR reaction or denaturation reaction can be carried out in each of the sample solution chambers without changing the temperatures of the other chambers. To move the position of the substrate 1 to be observed through the objective lens 15, the cell 7 is fixed on rails 742, 743 and 744 by jig 741 and can be arbitrarily transferred on a two-dimensional plane by a stepping motor (not shown).

Figure 9A:
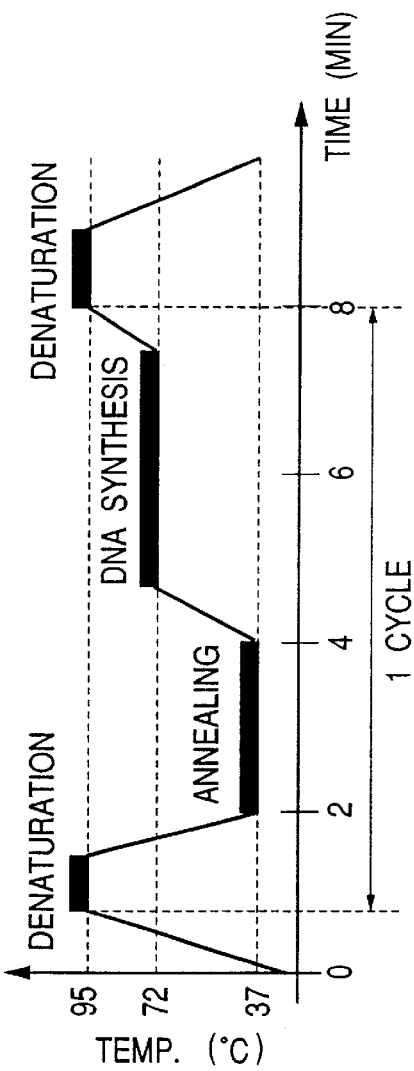
Figure 9C:
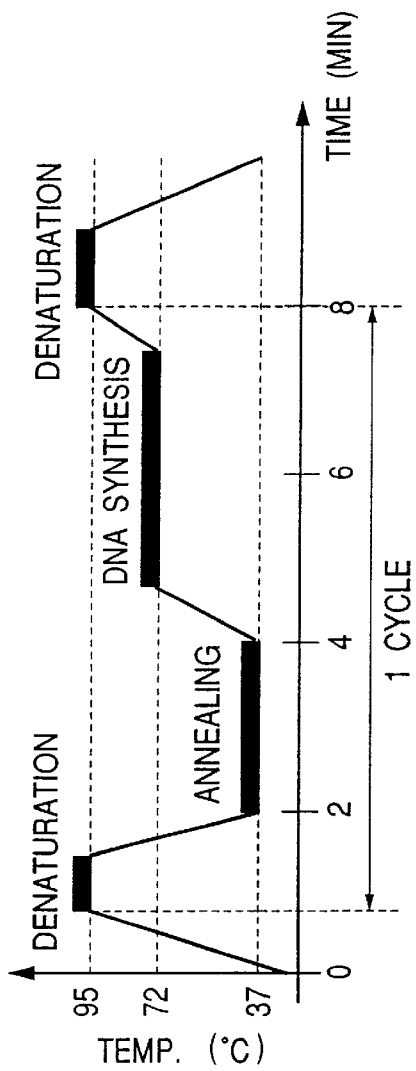

FIGS. 9A through 9C illustrate timetables demonstrating a polynucleotide separation process using the polynucleotide separation cell shown in FIGS. 6–8. Initially, a sample solution containing polynucleotides introduced into the sample solution chamber 731 is subjected to PCR amplification as a pretreatment by applying a total of about 20 to 30 cycles of chronological changes in temperature to the solution as shown in FIG. 9A. In other words, double stranded-polynucleotides are denatured into single stranded-polynucleotides in the first denaturation process. Annealing with probes in the sample solution and subsequently polymerase elongation are then conducted, and these processes are repeated to amplify polynucleotides. The temperatures in the processes are controlled on the whole sample solution in the sample solution chamber 731 by the Peltier device 32. From the sample solution containing the amplified polynucleotides, a polynucleotide having a specific base sequence is extracted by means of process as shown in FIG. 9B. To be more specific, in the sample introduction process, polynucleotides in the sample solution in the sample solution chamber 731 are induced to the sample solution chamber 732 by setting the electrodes 751 and 755 as cathodes and the electrode 754 and the electrode above the substrate 1 as anodes. The sample solution in the sample solution chamber 732 is then heated to 95° C. by the Peltier device 34 to disassociate hydrogen bonds in polynucleotides in the sample solution to form single stranded-polynucleotides. The single stranded-polynucleotides are then hybridized to probes in the target polynucleotide hybridization area on the substrate 1 by cooling the solution to a temperature of 37° C. Remained polynucleotides in the sample solution not hybridized to the probes in the hybridization areas are then returned to the sample solution chamber 731 by setting the electrode 751 as an anode. The cell is then subjected to fluorescence observation to identify to which area on the substrate 1 the target oligonucleotide is hybridized. On the basis of information of an area where the target polynucleotide is hybridized to the probes on the substrate 1 (output of the fluorescent emission intensity detector 191 shown in FIG. 2), the target polynucleotide hybridized to the probe in a target polynucleotide hybridization area on the substrate 1 can be dissociated from the probe by irradiating a convergent light to the area. In this process, an alternating field is applied between the electrode 753 and the electrode 131 on the surface of the substrate 1 to elongate the target polynucleotide. In addition, the target polynucleotide in the specific target polynucleotide hybridization area on the substrate 1 alone is denatured by supplying the convergent light 51 from the lens 15, while setting the electrode 755 as an anode, and thus the objective target polynucleotide alone is introduced into the sample solution chamber 733. By setting the electrode 752 as a cathode while retaining the electrode 751 as an anode, polynucleotides in the sample solution in the sample solution chamber 731 which have not been hybridized to the probes are retained in the sample solution chamber 731 without transferring to the sample solution chamber 732 or 733. Components required for PCR are then introduced through the solution inlet 713 to the sample solution chamber 733 while continuously applying an electric field to the electrodes. About 20 to 30 cycles of aftertreatment shown in FIG. 9C are then carried out to extract and amplify an objective polynucleotide selectively with a high precision and a high speed from the sample solution introduced into the sample solution chamber 733. After extracting the amplified sample solution in the sample solution chamber 733, each of polynucleotides hybridized to each of the areas can be selectively extracted and amplified in sequence by moving the substrate 1 and repeating the separation process shown in FIG. 9B and the aftertreatment PCR process shown in FIG. 9C in a similar manner as above.

Specific procedures for decreasing the temperatures are not described in the timetables shown in FIGS. 9A through 9C, whereas cooling of individual chambers can be conducted in a short time by positively using the Peltier devices 32, 34 and 35 in FIG. 6 for heat dissipation. Such Peltier devices can be provided separately in individual target polynucleotide hybridization areas for cooling after the area specific denaturation for denaturing polynucleotides hybridized to the probes of the target polynucleotide hybridization area.

EMBODIMENT II

Embodiment II is essentially identical with Embodiment I except that the former utilizes heating elements embedded in the substrate 1 for temperature control of individual target polynucleotide hybridization areas to denature the target polynucleotide hybridized to the probes, instead of the convergent light irradiation in the latter. The present embodiment will now be described in detail with reference to FIGS. 10 through 15.

FIG. 10 illustrates the relationship between substrate 1 having a target polynucleotide hybridization area and an optical system for detecting hybridization in the target polynucleotide hybridization area, according to the second embodiment of the invention. Comparison between FIG. 10 and FIGS. 2 and 3 demonstrates that the substrate according to the present embodiment comprises substrate base 13 composed of electrically conductive film 131 having target polynucleotide hybridization areas on its surface, temperature control unit 133 and thermally conductive insulting substrate 132. On the surface of the electrically conductive film 131 are provided a plurality of target polynucleotide hybridization areas 141, 142, 143, 144, 145 and 146, and inside of the temperature control unit 133 are embedded electrodes and heating elements to evolve heat by the electrodes, for independently controlling the temperatures of individual target polynucleotide hybridization areas separately. Each of the target polynucleotide hybridization areas has a dual-layer structure composed of probe hybridization layer 221 such as an aluminum oxide thin film layer, and electric insulator layer 222. Probes (oligonucleotides) 41, 42, 43, 44, 45 and 46 each having a length of 8–9 bp are respectively immobilized to the surface of each of the target polynucleotide hybridization areas. FIG. 10 schematically illustrates the state where complementary target polynucleotides 41', 42', 43' and 46' alone are respectively hybridized only to the probes 41, 42, 43 and 46 of these probes.

When the present embodiment is configured such that a fluorescent dye is attached simultaneously at the time when the target polynucleotides 41', 42', 43' and 46' are hybridized to probes 41, 42, 43 and 46, the magnitude of hybridization between the probe and target polynucleotide in each area can be estimated through fluorescence emission intensity by exciting the fluorescent dye and detecting fluorescence emitted from the dye. In addition, area specific temperature increase in the target polynucleotide hybridization areas can be determined by using the phenomena where the fluorescence emission intensity of a fluorescent dye decreases in proportion to an increasing temperature through the function of the thermal quenching effect. The temperatures of target polynucleotide hybridization areas can be estimated by analyzing the fluorescence emission intensity changes of the fluorescent dye based upon its temperature dependency. The identical or equivalent elements to those of EMBODIMENT I are indicated with the same reference numerals in the present embodiment.

Figure 11:
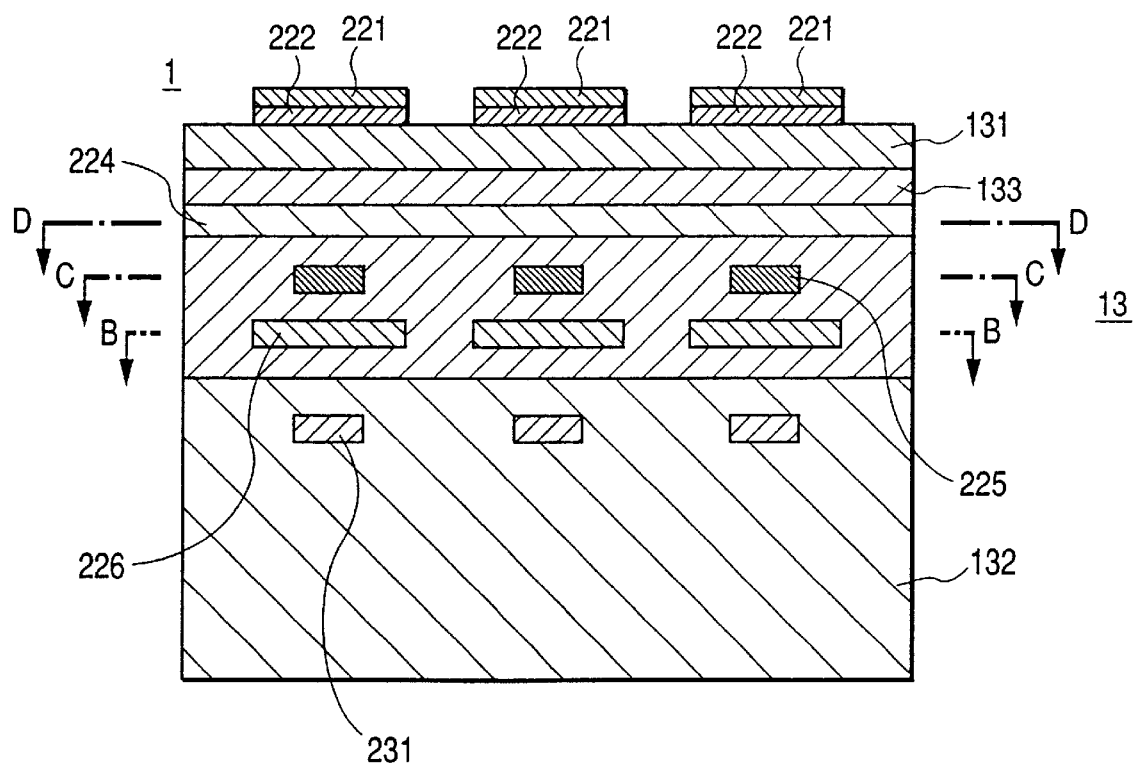
FIG. 11 is a sectional view along with the lines A—A of the substrate 1 shown in FIG. 10.

FIG. 11 is a sectional view of the substrate 1 shown in FIG. 10 along with the lines A—A. Substrate 1 has a laminate structure composed of thermally conductive insulating substrate 132, temperature control unit 133 and electrically conductive film 131. On the surface of the top layer, electrically conductive film 131, is formed a dual-layer structure of probe hybridization layer 221 to be target polynucleotide hybridization area, and electrically insulating layer 222. Below the temperature control unit 133 are formed layers of planar electrodes 226, heating elements 225 and planar electrodes 224. Individual electrodes in the planar electrode 226 and the planar electrode 224 are in the shape of cross-matrix such that individual crossing points separately correspond to the position of individual heating elements and to positions of individual target polynucleotide hybridization areas. Thermistors 231 for temperature measurement are embedded in the thermally conductive insulating substrate 132 corresponding to each of the target polynucleotide hybridization areas, by which the temperature of each of the hybridization areas can be determined.

Figure 12A:
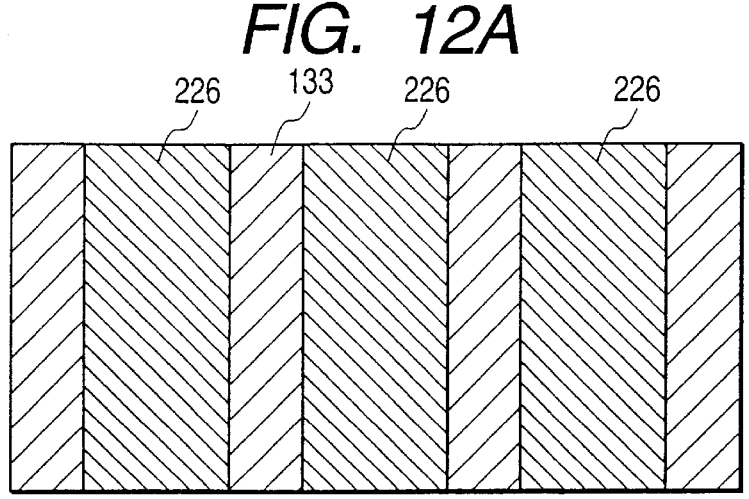
FIGS. 12A, 12B and 12C are sectional views along with the lines B–B', C—C and D–D, respectively, of a temperature control unit 133 of the substrate 1 according to the second embodiment.
Figure 12B:
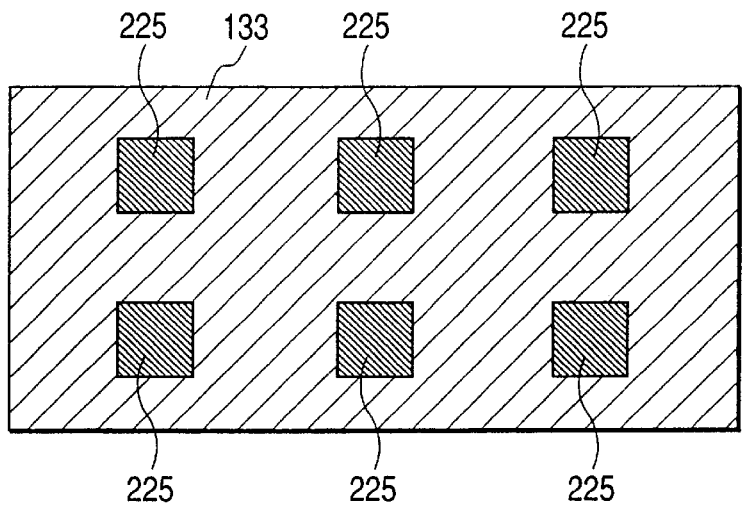
Figure 12C:
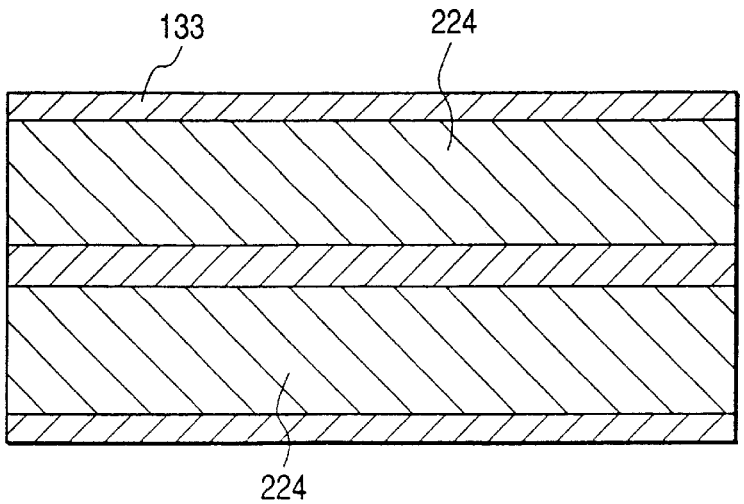

FIGS. 12A through 12C are sectional views of the temperature control unit 133 of the substrate 1 according to the second embodiment along with the lines B—B, lines C—C and lines D—D, respectively. The planar electrodes 226 are orthogonal to the planar electrodes 224, and individual crossing points therebetween sandwich each of the heating element layers 225. Consequently, a heating element layer 225 alone at a crossing point of a planar electrode 226 and a planar electrode 224 can evolve heat by selectively applying a potential difference between the above planar electrode 226 and the above planer electrode 224 to pass an electric current. In other words, by selecting a planar electrode 226 and a planar electrode 224 properly and applying a potential difference therebetween, the temperature of a specific target polynucleotide hybridization area corresponding to the crossing point between these selected electrodes can be increased.

The substrate 1 shown in FIG. 10 can be used in place of the substrate 1 of the polynucleotide separation cell 7 shown in FIGS. 6 through 8, whereas a simpler embodiment will be described herein.

Figure 13:
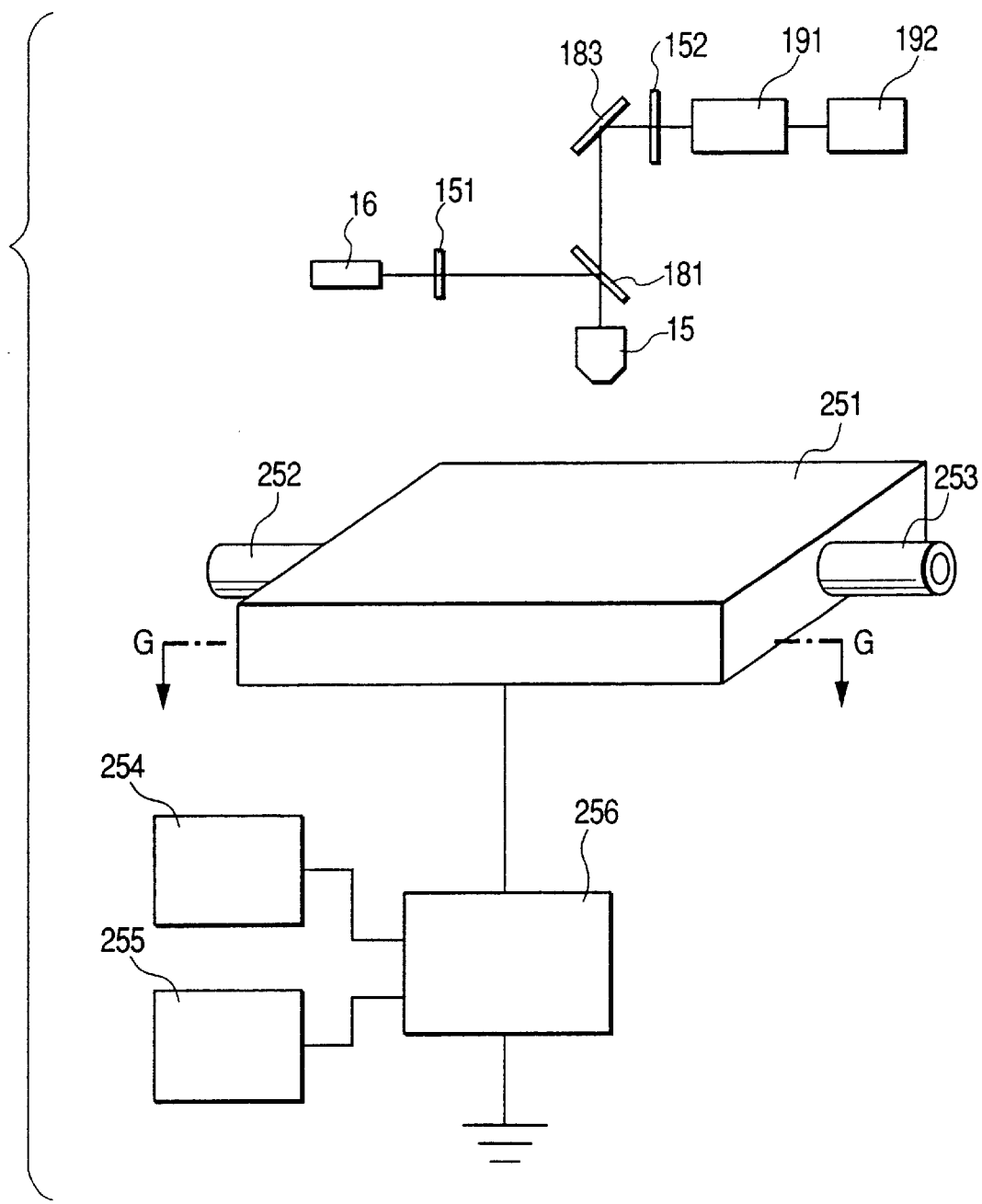
FIG. 13 is a block diagram illustrating a polynucleotide separation cell 251 and related devices thereto according to the second embodiment.
Figure 14:
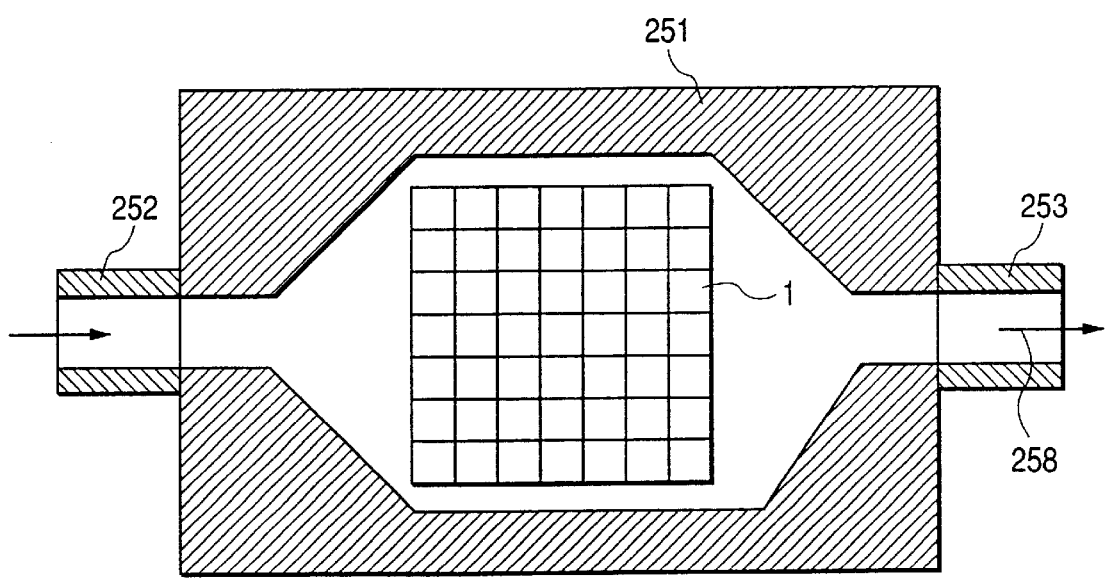
FIG. 14 is a sectional view along with the lines G—G of the polynucleotide separation cell 251 according to the second embodiment.

FIG. 13 is a block diagram illustrating a polynucleotide separation cell 251 and related devices thereto, and FIG. 14 is a sectional view of the polynucleotide separation cell 251 along with the lines G—G, each according to the second embodiment. The polynucleotide separation cell 251 is composed of a light-transmittable case to permit optical observation of the substrate 1 in the cell. To the cell 251 are connected sample solution injection tube 252 for injecting a sample solution containing polynucleotides, and extraction tube 253 for extracting the target polynucleotide hybridized to a specific target polynucleotide hybridization area on the substrate 1, through which the solution can be passed in the direction indicated by arrows 57 and 58. Above the cell 251 is provided transparent electrode (not shown) for applying a potential difference between the transparent electrode and the electrically conductive film 131 of the substrate 1. The present embodiment includes direct current power source 254, alternating current power source 255 and control circuit 256 for allowing a heating element corresponding to a specific target polynucleotide hybridization area to evolve heat or for generating a DC field or alternating field in the target polynucleotide hybridization area. The state of the substrate 1 can, therefore, be controlled on the basis of temperature information from the thermistors 231 according to procedures mentioned below.

Figure 15:
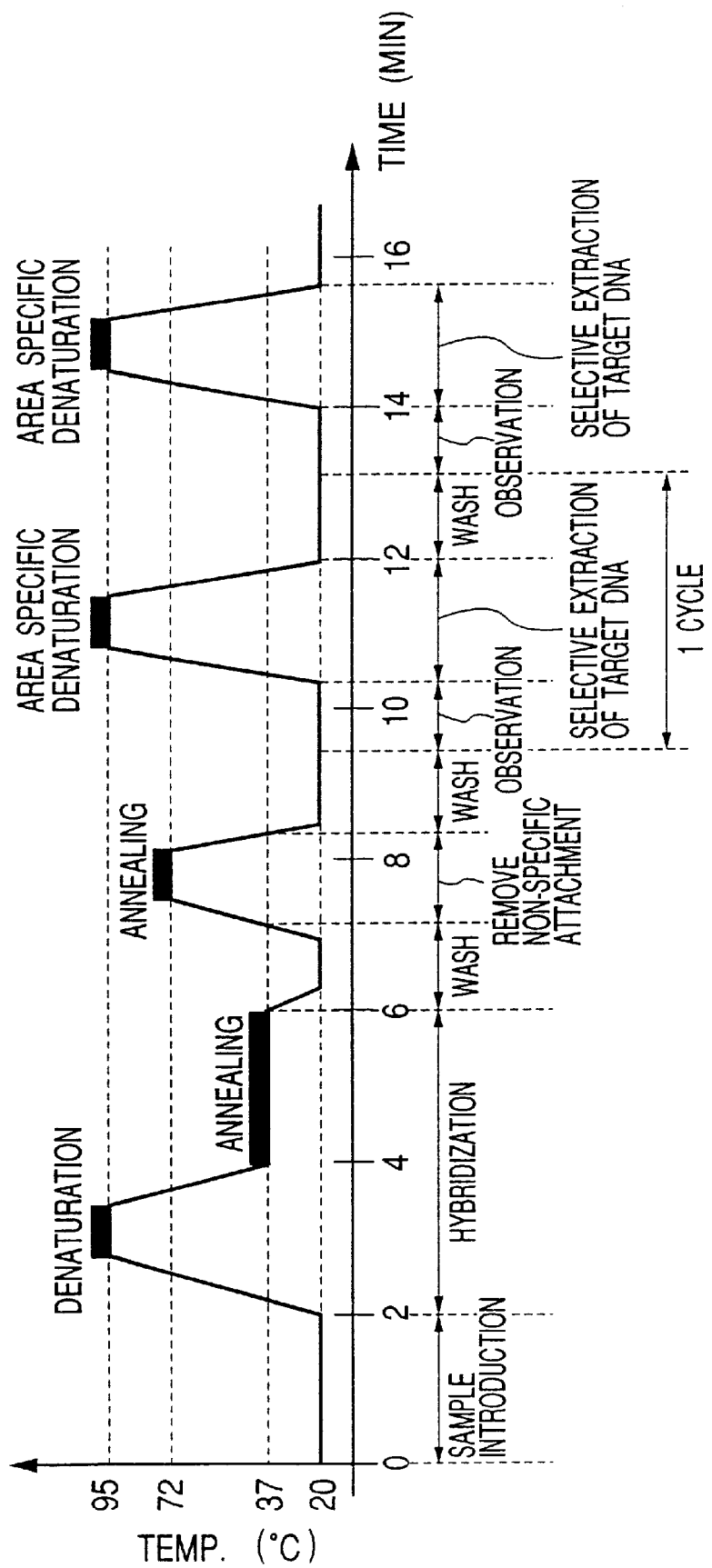
FIG. 15 is a timetable demonstrating the separation process in the polynucleotide separation cell according to the second embodiment.

FIG. 15 is a timetable illustrating a separation process in the polynucleotide separation cell according to the second embodiment.

From a sample introduced into the cell 251, a polynucleotide having a specific base sequence is singly extracted in the process shown in FIG. 15.

(1) In the sample solution introduction process, polynucleotides in the solution are induced to the surface of the substrate 1 by setting the electrically conductive film 131 of the substrate 1 as an anode and the transparent electrode on the upper surface of the cell as a cathode. Separately, polynucleotides can be elongated by generating an alternating field between the electrically conductive film 131 of the substrate 1 and the transparent electrode on the upper surface of the cell. In this step, the surface temperature of the substrate 1 is increased up to 95° C. by allowing all electrodes 224 and 226 to be connected and to thereby all heating elements 225 to evolve heat, each in the temperature control unit 133.

(2) The temperature is then decreased to 37° C. This procedure allows the probes immobilized on the target polynucleotide hybridization areas to hybridize to the target polynucleotides in the sample solution.

(3) Next, the surface layer of the substrate 1 is heated up to about 72° C., and the electrically conductive film 131 of the substrate 1 and the transparent electrode on the upper surface of the cell are respectively set to a cathode and an anode so as to remove, together with the sample solution, polynucleotides non-specifically hybridized to probes.

(4) After replacing the solution in the cell 251 with a new one, each one of the electrodes 224 and 226 is respectively allowed to be connected, and one of the heating elements 225 is allowed to evolve heat, each in the temperature control unit 133 to increase the temperature of one of the target polynucleotide hybridization areas up to 95° C., thereby the target polynucleotide hybridized to probes in this area is denatured and extracted with the solution.

(5) By repeating similar procedures on each of the target polynucleotide hybridization areas, each of target polynucleotides hybridized to probes in individual areas can be extracted in sequence.

In this case, the processing efficiency can be enhanced by detecting, beforehand, hybridization state of target polynucleotides on individual target polynucleotide hybridization areas, on the basis of temperature information from the detector 191 and the analyzer 192 and conducting the temperature control only on an area to which a polynucleotide to be extracted is hybridized, as described in EMBODIMENT I.

EMBODIMENT III

EMBODIMENT III relates to a configuration of substrate 1 having target polynucleotide hybridization areas which are designed to immobilize probes with stability. To be more specific, the present embodiment proposes the substrate 1 having a configuration in which the surfaces of hybridization areas are fabricated of oxidized metal films and the probes can be immobilized with stability by a silane coupling reaction.

The substrate 1 according to the present embodiment may be prepared in the following manner: A 0.4-mm thick and 24-mm square glass substrate is immersed in an NaOH (1 M) solution and subjected to ultrasonic cleaning for 30 minutes. The cleaned substrate is washed with running ultrapure water and thereafter baked at 110° C. for 15 minutes. Using a vacuum metallizer, chromium (Cr) is vacuum-deposited on the substrate in a thickness of 3 nm, and the deposited substrate is washed with ethanol. After immersed in 3-glycidoxypropylmethoxysilane (not diluted) for 5 minutes, the substrate is immersed in a 4% 3-glycidoxypropylmethoxysilane solution in 50% ethanol medium for 30 minutes with stirring at times. The substrate is then taken out from the solution and baked at 110° C. for 30 minutes to introduce glycidoxy groups onto the surface of the metal through the silane coupling reagent, and thereby substrate 1 is obtained.

Figure 16:
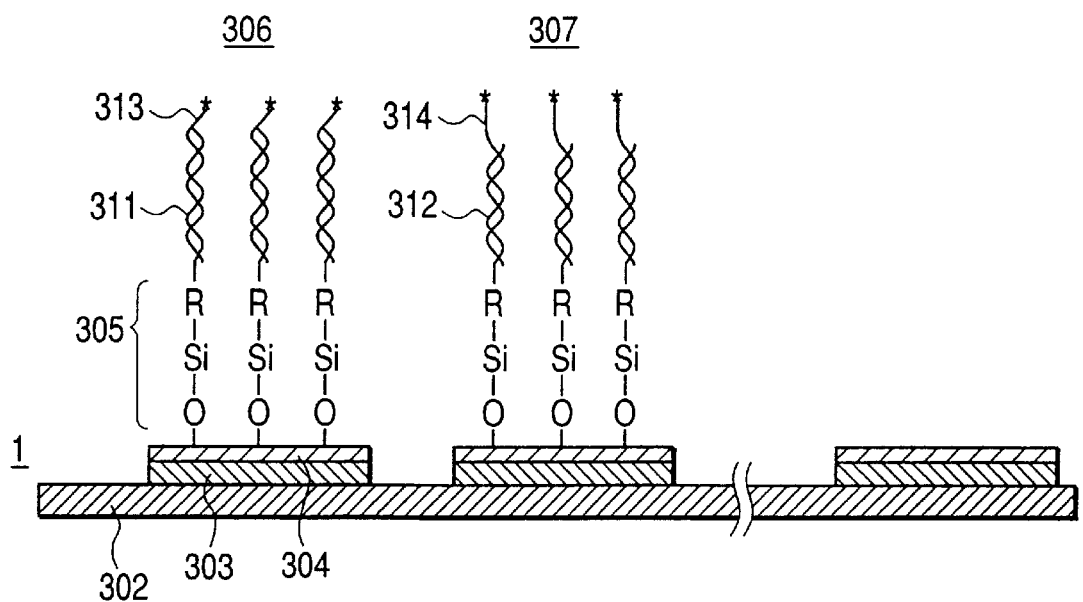
FIG. 16 is a diagram illustrating stable immobilization of probes on a substrate 1 according to a third embodiment of the invention.

FIG. 16 illustrates the stable immobilization of probes on a substrate 1 according to EMBODIMENT III. The substrate 1 according to the present embodiment is composed of glass substrate 302, Cr layers 303 deposited on the substrate 302, which surfaces constitute oxidized films 304. Probes are immobilized through silane coupling layers 305. To verify that the probes are immobilized with stability according to the present embodiment, polynucleotides respectively having lengths of 521 bp and 625 bp, whose ends are labeled with fluorescent dye sulforhodamine 101, are hybridized to probes 311 and 312, which probes are respectively immobilized through silane coupling layer 305 on target polynucleotide hybridization areas 306 and 307.

A comparative test to verify the advantages of the substrate 1 according to EMBODIMENT III will be described below.

Initially, comparison was conducted among the substrate according to EMBODIMENT III, a substrate obtained by vacuum-depositing aluminium (Al) instead of Cr on the surface of glass 302, and a substrate obtained by subjecting the surface of glass 302 directly to silane coupling. As the substrate according to the present embodiment, two substrates were prepared by vacuum-depositing Cr on the whole surface of glass 302 in a thickness of 5.4 nm. These substrates had light transmittance at 600 nm to 800 nm of 53% to 56%. The Al-deposited substrate was obtained by vacuum-depositing Al instead of Cr on the whole surface of glass 302 in a thickness of 15 nm in a similar manner to that in the embodiment. The substrate had a light transmittance at 600 nm to 800 nm of 19 to 25%. Glass itself without deposition of a metal film has a light transmittance at 600 nm to 800 nm of about 84%. Within these ranges of transmittance as above, a target polynucleotide hybridized to a probe can be detected through fluorescence emitted by exciting the target polynucleotide labeled with a fluorescent dye such as the sulforhodamine 101 (absorption maximum 594 nm, fluorescence 615 nm) by exciting light derived from argon (Ar, 514 nm) or helium-neon (He—Ne, 545 nm).

Figure 17A:
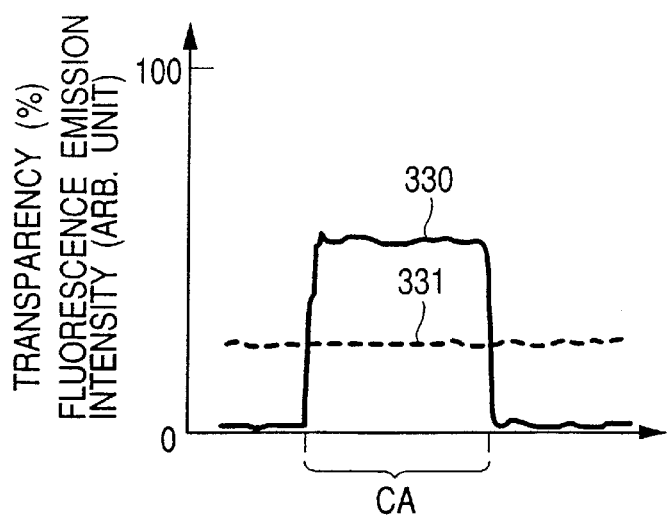
FIGS. 17A, 17B and 17C are diagrams respectively illustrating test results for verifying the advantages of the substrate according to the third embodiment.
Figure 17B:
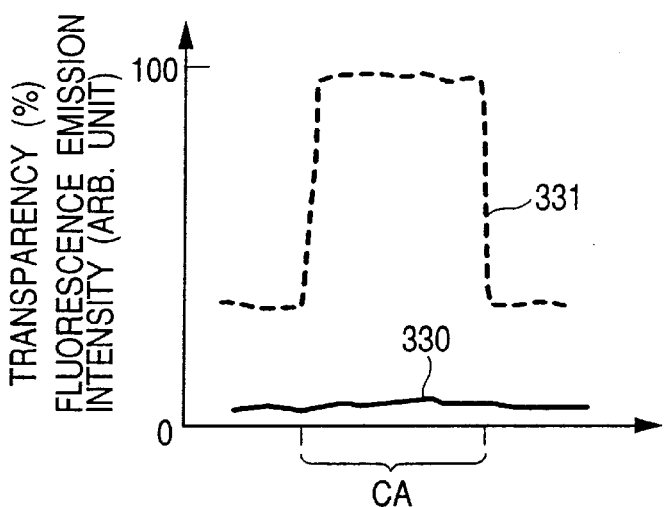
Figure 17C:
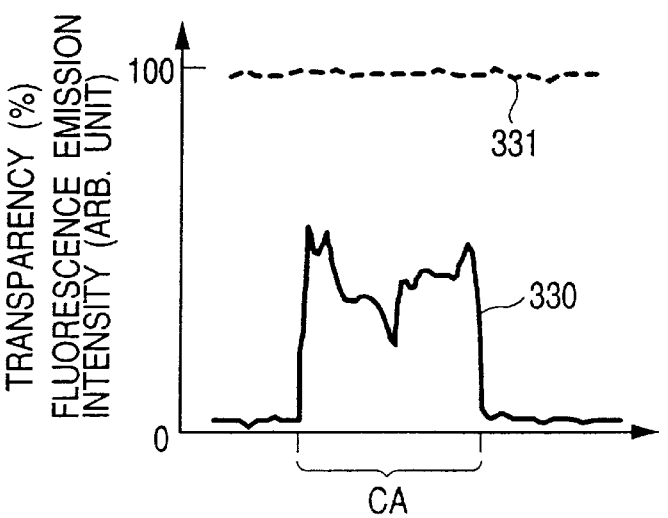

FIGS. 17A through 17C are diagrams illustrating results of tests to verify the advantages of the substrate according to EMBODIMENT III.

Using a series of tested substrates, polynucleotides respectively having lengths of 521 bp and 625 bp, whose ends were labeled with fluorescent dye sulforhodamine 101 were hybridized to probes 311 and 312, which probes had been respectively immobilized through silane coupling layer 305 on each of the tested substrate. The treated substrates were subjected to laser confocal microscopic scanning, and the resultant relative fluorescence emission intensity and transmittance are shown in FIG. 17A for a substrate according to EMBODIMENT III obtained by vacuum-depositing Cr 5.4 nm thick, FIG. 17B for a substrate obtained by vacuum-depositing Al 15 nm thick instead of Cr, and FIG. 17C for a substrate having no deposited metal film. In the figures, the abscesses indicate the scanning position on the substrate, and the vertical axes indicate, by solid line 330, fluorescence emission intensity (equal to or more than 580 nm) distribution and transmitted light intensity distribution detected with the laser microscope; and the broken line 331 indicates transmittance distribution at wavelengths from 380 nm to 450 nm.

FIG. 17A demonstrates that a constant fluorescence emission intensity 330 could be obtained all over the area CA where the polynucleotide labeled with the fluorescent dye sulforhodamine 101 was hybridized, in the substrate according to EMBODIMENT III. The fluorescence emission intensity 330 in the other positions was sufficiently low. The transmittance at 380 nm to 450 nm was almost constant in any positions, indicating that the Cr layer was retained with stability and was not delaminated from the surface of glass 302 over the reactions and procedures from immobilization of probes to hybridization of the target polynucleotide.

FIG. 17B for the Al-deposited substrate instead of Cr deposition demonstrates that, the transmittance of the area CA where the polynucleotide labeled with the fluorescent dye sulforhodamine 101 was to be hybridized was remarkably high, indicating that the Al-deposited surface had been dissolved in the immobilization of the probes. In other words, the Al-deposited surface was dissolved in a 10 mM Tris-hydrochloric acid-1 mM EDTA buffer solution (pH 7.5) which is a generally used medium for dissolving DNA and/or RNA, indicating that such an Al-deposited substrate cannot be used in reaction systems using aqueous solutions. Consequently, in this tested substrate, the probes were not substantially immobilized, hence the polynucleotide labeled with the fluorescent dye sulforhodamine 101 was not hybridized, and the fluorescence emission intensity was significantly low globally.

As is shown in FIG. 17C for the substrate where the probes were immobilized by subjecting the surface of the glass directly to silane coupling, the area CA where the polynucleotide labeled with the fluorescent dye sulforhodamine 101 was hybridized had a higher fluorescence emission intensity 330 than the other positions where no probes were immobilized, indicating that the substrate served to immobilize the probes. The fluorescence emission intensity 330 in this substrate fluctuated, however, by location as compared with the substrate according to the present embodiment, indicating that the probes were not immobilized homogeneously.

The above results demonstrates that the Cr-deposited substrate according to the present embodiment is advantageous for stable immobilization of probes and for hybridization of target polynucleotides. In addition to Cr-deposited substrates, any substrates each obtained by vacuum depositing a metal, which is stable in a weak alkali solution, on a glass substrate in a thickness of several nanometers to 10 nm are advantageous. To be more specific, those covered with a film of oxide on the surfaces and hardly dissolved in a weak alkali solution at 95° C. are desirable, whereas gold and platinum cannot be used since they form no oxide film and hence silane coupling cannot be done. Stainless steel has similar characteristics to Cr such as to be stable in a weak alkali solution and to form an oxide film, but it is excluded from the scope, since it does not allow active residues to be introduced by silane coupling for some unknown reasons. Similar examinations have revealed that at least any metal of Ti, V, Cr, Fe, Co, Ni, Mo and W is effective and advantageous.

Figure 18A:
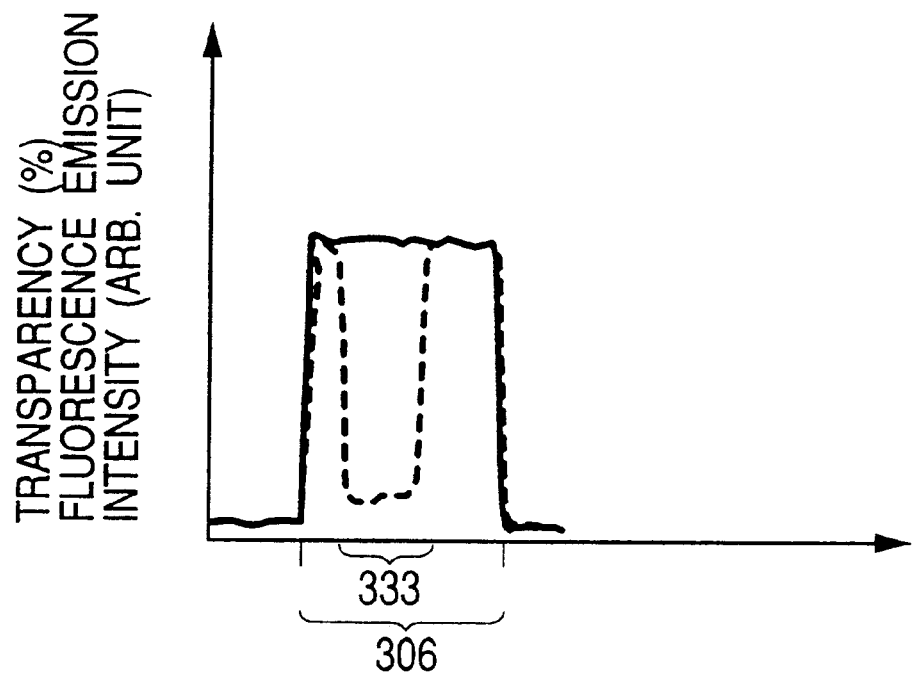
FIGS. 18A and 18B are diagrams illustrating efficient extraction of a target oligonucleotide hybridized to a probe on the substrate according to the third embodiment.
Figure 18B:
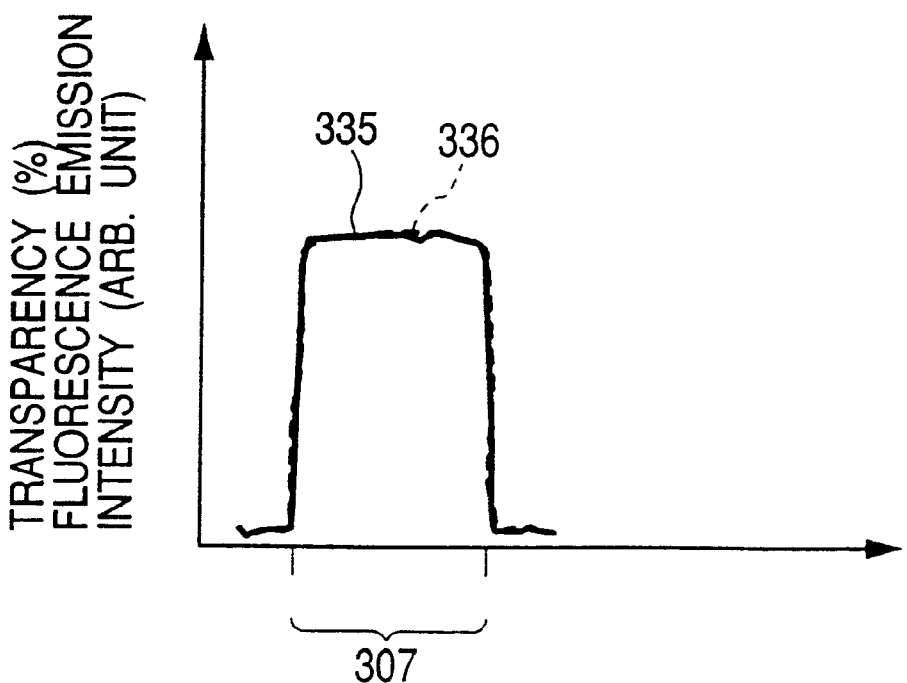

Next, explanation will follow concerning that a target polynucleotide hybridized to a probe on the substrate according to the present embodiment can be efficiently extracted, with reference to FIGS. 18A and 18B. FIGS. 18A and 18B respectively illustrate the results of tests where polynucleotides respectively having lengths of 521 bp and 625 bp, whose ends were labeled with fluorescent dye sulforhodamine 101, were hybridized to probes 311 and 312, which probes were respectively immobilized through silane coupling layer 305 on the areas 306 and 307 shown in FIG. 16. The surface of each tested substrate was covered with 20 microlitter of a 20 mM Tris-hydrochloric acid buffer (pH 7.5).

FIGS. 18A and 18B respectively demonstrate the results obtained by laser scanning (514 nm) over the areas 306 and 307 separately and detecting fluorescence emission intensity (510 nm to 580 nm), with the abscissa indicating scanning positions on the substrate and the vertical axis indicating relative fluorescence emission intensity distribution detected through a laser microscope. Line 335 represents the relative fluorescence emission intensity, indicating that a nearly constant fluorescence was detected all over the both areas 306 and 307. Next, the area 306 alone was subjected to scanning with 10 mW YAG laser (spot diameter 5 nm) at 1053 nm. As shown in FIG. 18A, the fluorescence emission intensity after scanning was decreased to about one-tenth at the region 333 which scanned with YAG laser, as indicated by broken line 336. In the area 307, both fluorescence emission intensities 335 and 336 did not change.

Figure 19:
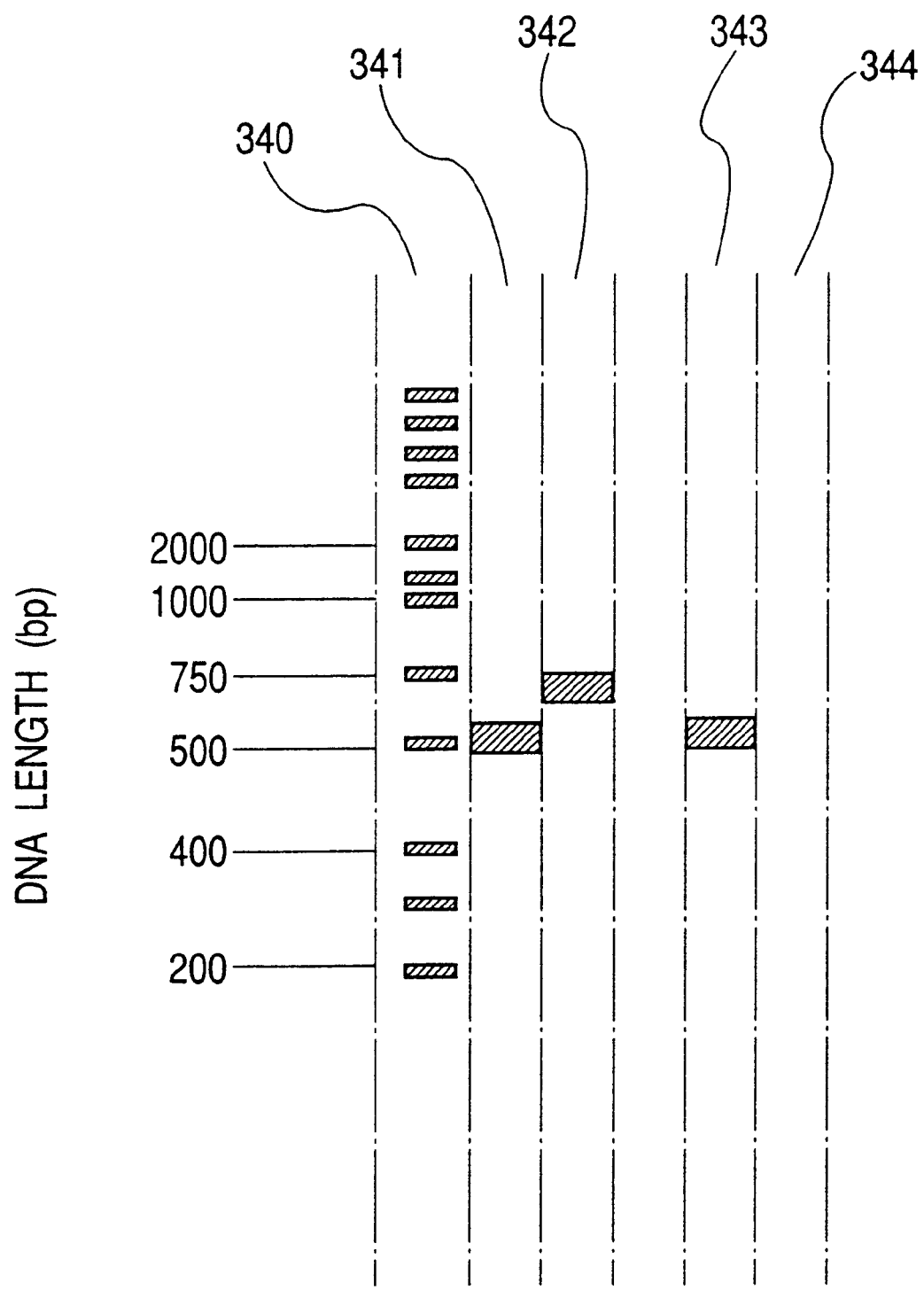
FIG. 19 is a diagram schematically illustrating results of electrophoresis, demonstrating the fractionation of a double stranded-polynucleotide according to the third embodiment.

FIG. 19 schematically illustrates results of electrophoresis concerning fractionation of polynucleotides according to the present embodiment.

Lane 340 is a lane of a marker. Lanes 341 and 342 demonstrate the results of electrophoresis on identical polynucleotides with those obtained in the areas 306 and 307 of the substrate 1 respectively. Bands of 521 bp and 625 bp are clearly observed in the lanes 341 and 342, respectively. Lanes 343 and 344 demonstrate the results obtained by scanning the area 306 of the substrate 1 with 10-mW YAG laser (spot diameter 5 nm) at 1053 nm, recovering the buffer on the surface of the scanned substrate 1, subjecting the buffer for PCR amplification, and subjecting the PCR amplification products to 2% agarose gel electrophoresis analysis. A band of 521 bp is clearly detected in the lane 343, whereas no band of 625 bp is detected in the lane 344, indicating that only the polynucleotide denatured from the area 306, which has been scanned with 10-mW YAG laser (spot diameter 5 nm), is present in a solution obtained by subjecting the recovered buffer to PCR amplification. According to the present embodiment, immobilization of probes and an efficient fractionation of hybridized polynucleotides can be achieved.

EMBODIMENT IV

EMBODIMENT IV is designed to utilize the inside wall of a capillary for minimizing the amount of a sample solution required for fractionation of polynucleotides, whereas the substrate 1 each in the above EMBODIMENTS I through III is plane-shaped.

Figure 20:
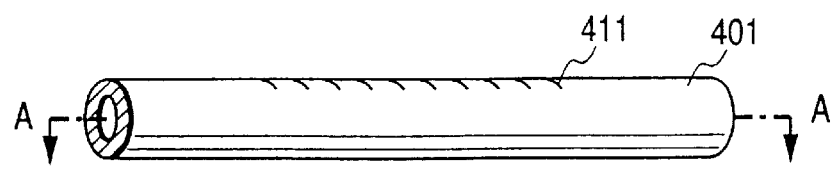
FIG. 20 is an external view of a capillary applicable to a fourth embodiment of the invention.
Figure 21:
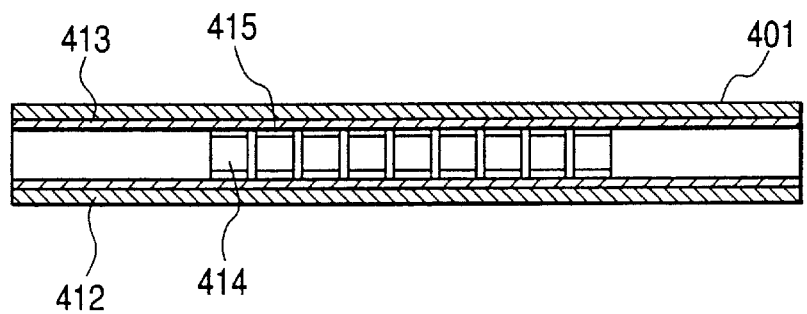
FIG. 21 is a sectional view along with the lines A—A of the capillary applicable to the fourth embodiment.

FIGS. 20 and 21 illustrate an external view and a sectional view along with the lines A—A of a capillary applicable in the fourth embodiment.

Capillary 401 is a light transmittable capillary such as a glass capillary. Inside of capillary wall 412 is coated with inner coat 413 composed of Cr or other metal exemplified in EMBODIMENT III. The surface of the inner coat is composed of a stable oxide formed by air oxidation of the metal. On the surface of the coat are cylindrically placed target polynucleotide hybridization areas 414, 415 . . . on which probes are immobilized. Area specific probes are closely immobilized on each of the target polynucleotide hybridization areas 414, 415 . . . Of polynucleotides in a sample solution, only each of polynucleotides complementary to each of the probes can be hybridized to each of the areas. On the external surface of the capillary 401 are indicated markers 411 at the boundary between the individual areas so as to ensure the observation of the positions of individual target polynucleotide hybridization areas from the outside of the capillary.

Figure 22:
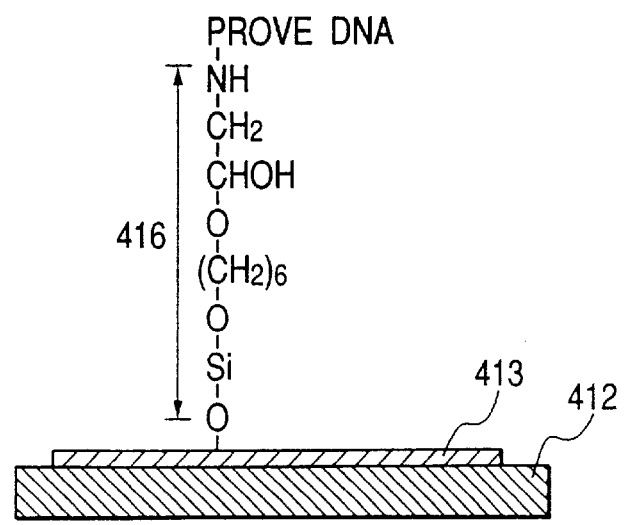
FIG. 22 is a diagram of an illustrative configuration for immobilizing a probe to a target polynucleotide hybridization area.

FIG. 22 is a diagram of an illustrative configuration for immobilizing a probe on a target polynucleotide hybridization area.

Independent oligonucleotide probe layers can be formed concentrically in the inner wall of a capillary, as illustrated in FIG. 21, for example, in the following manner: Initially, epoxy groups 416 are formed all over areas on the inner wall of the capillary 401 by reacting the whole inner wall of the capillary with a divalent reagent having silanol group and epoxy group at both ends to make the inner wall water repellent and thereby reject an aqueous sample solution. Next, a nucleotide sample solution to be hybridized to a specific area 415 is introduced as a drop into the capillary 401. The drop becomes spherical and in concentric contact with the inner wall with a minimum contact area because of the water repellency of the inner wall of the capillary. The drop is then introduced to the area 415 and left for a while to make a free end of the epoxy group 416 to hybridize to an oligonucleotide probe, which 5-end has been modified with an amino group. The drop containing the reacted nucleotide probe is taken out of the capillary 401 immediately after the completion of the reaction. By repeating procedures in which a different sample drop is introduced to react in another area in a similar manner, the configuration shown in FIG. 21 can be obtained.

The timetable for fractionating target polynucleotides in a sample solution according to the fourth embodiment is not described herein as it is identical with the timetable shown in FIG. 15.

Figure 23:
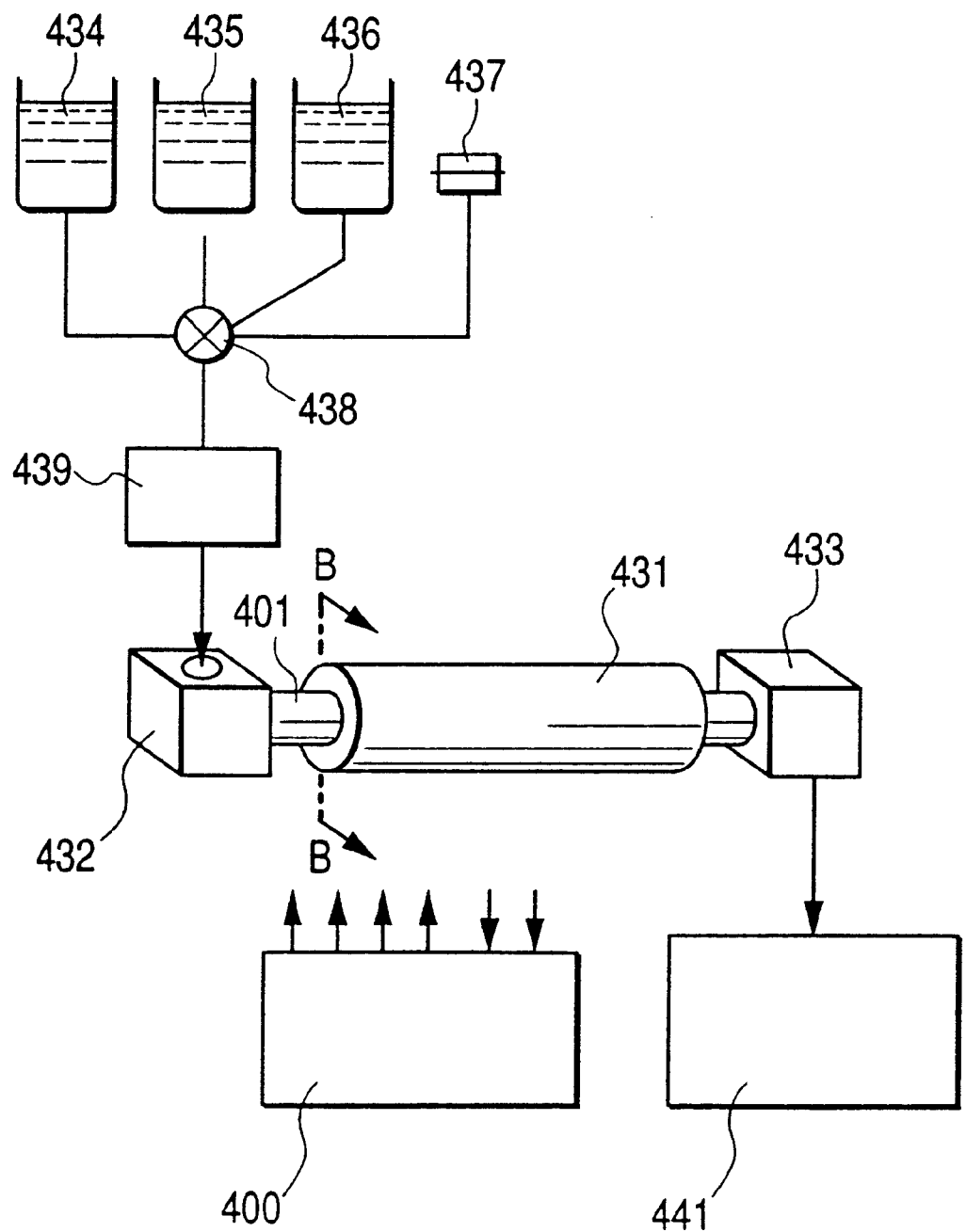
FIG. 23 is a general view of the configuration of a polynucleotide separation apparatus according to the fourth embodiment.

FIG. 23 is a general view of the configuration of a polynucleotide separation apparatus according to the fourth embodiment. In the inside of polynucleotide separation module 431 is integrated the capillary 401 described in FIGS. 20 and 21. Both ends of the capillary 401 are separately connected to capillary connection units 432 and 433. One of a sample solution retained in reservoir 434, a washing solution retained in reservoir 435, a washing solution retained in reservoir 436 and air passing through air filter 437 is selected by selector 438, and introduced into the capillary connection unit 432 with pump 439. Controller 400 represents a control and power supply means according to the apparatus of the present embodiment. The solution extracted from the polynucleotide separation module 431 passes through the capillary connection unit 433 and is supplied to aftertreatment process 431 including PCR amplification. To the controller 400 are collected necessary data from individual units of the apparatus, and necessary operation signals in accordance with the data are sent to individual units from the controller. Details of a practical configuration and connection to individual units of the apparatus are omitted herein. These can be achieved by one skilled in the art based upon the aforementioned timetables and the following descriptions.

Figure 24:
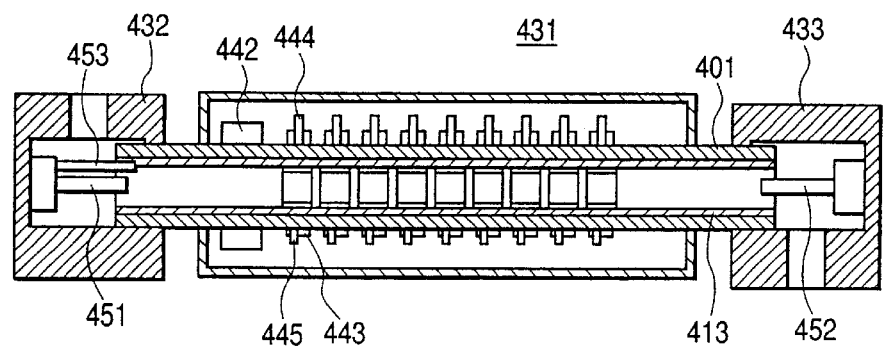
FIG. 24 is a sectional view along with the lines B—B of a polynucleotide separation module 431 of the fourth embodiment.

FIG. 24 is a sectional view along with the lines B—B of the polynucleotide separation module 431 of the fourth embodiment. In the inside of the module 431 are provided, in parallel, light source 442 for introducing a light to the wall of the capillary 401; doughnut-shaped heat sources 443 corresponding to individual target polynucleotide hybridization areas of the capillary 401; light detection probes 444 for detecting fluorescence emitted from a target polynucleotide hybridization area which is excited by an exciting light plasmon-excited from the capillary to the inside, or for detecting the markers 411 on the surface of the capillary; and thermal detection probes 445 for detecting the temperature of the capillary. Electrodes 451 and 452 are provided respectively in the capillary connection units 432 and 433 to extract sample DNA in the capillary 401 by electrophoresis. Electrode connector 453 is to apply an electric potential to the inner coat 413 of the capillary 401 so as to move nucleotides toward or away from the inner surface of the capillary.

Figure 25:
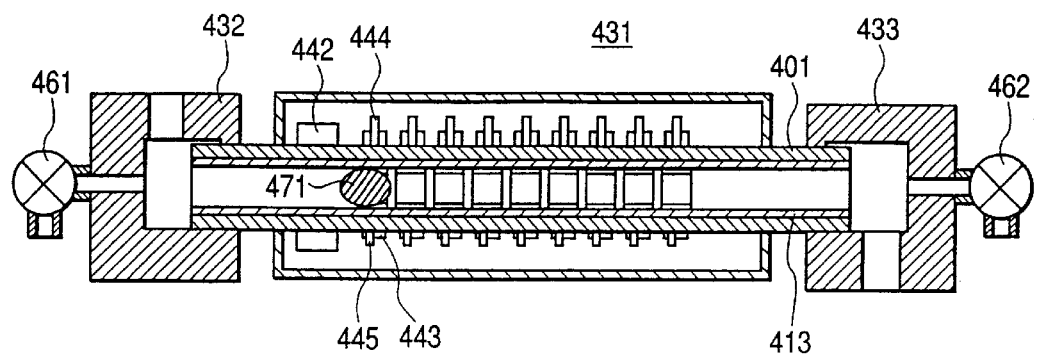
FIG. 25 is a diagram illustrating a variation of the polynucleotide separation module 431 according to the fourth embodiment shown in FIG. 24.

FIG. 25 illiterates a variation of the polynucleotide separation module 431 shown in FIG. 24 according to the fourth embodiment. The basic configuration of the variation is the same as in the embodiment shown in FIG. 24, except that the former employs drop 471 as a washing solution to be introduced for extracting a separated polynucleotide. The drop 471 is introduced from the reservoir 436 into the capillary 401 by adjusting the selector 438 shown in FIG. 23; the drop 471 is then pushed to an objective target polynucleotide hybridization area by air passing through the air filter 437 so as to cover the area. Next, leak valves 461 and 462 are opened to escape air in the capillary 401, which is expanded by area specific heat from the heat source 443, the position of the drop 471 is thus fixed. The temperature of the area is then increased to a temperature equal to or higher than the denaturation temperature to denature the target polynucleotide from the probe. Subsequently, the leak valves 461 and 462 are closed, and the drop 471 is pushed to the capillary connection unit 433 by the air passing through the air filter 437 so as to extract the target polynucleotide. According to the present embodiment, the drop come in contact with a specific target polynucleotide hybridization area alone, and contamination to the drop will not occur even if the temperature of other area reaches to the denaturation temperature. The extraction with a higher precision can, therefore, be achieved. In the present embodiment, area specific heating is carried out by one of the heat sources 443 in the polynucleotide separation module 431, whereas the extraction with a high precision can also be achieved by using one heat source in the shape covering all over the target polynucleotide hybridization areas.

Figure 26:
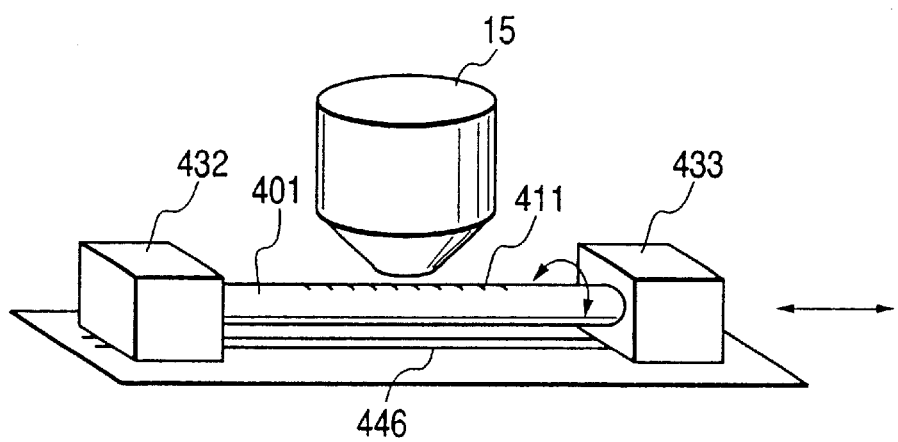
FIG. 26 is a diagram illustrating another variation of the polynucleotide separation module 431 according to the embodiment shown in FIG. 24.

FIG. 26 illustrates another variation of the polynucleotide separation module 431 according to the embodiment shown in FIG. 24. In the present embodiment, light source 442, heat source 443, light detection probe 444 and heat detection probe 445 each to be provided in the inside of the capillary 401 are omitted, and an optical system is provided in the exterior to the capillary 401 as an alternative to the above elements. In other words, the present embodiment employs the capillary 401 instead of the substrate 1 in the configuration shown in FIGS. 2 and 6 according to EMBODIMENT I. Consequently, the identical optical system with that in FIG. 2 can be employed, whereas only the objective lens 15 is shown in FIG. 26 for the simplification.

The capillary 401 connected to the capillary connection units 432 and 433 is moved on the rail 446 to observe the state of the inside of the capillary at a specific target polynucleotide hybridization area; and simultaneously a convergent light is irradiated to the aforementioned area of the capillary to heat area-specifically the vicinity alone of the convergent point in the capillary. When the capillary is designed to rotate in the circumferential direction, the state of the hybridization of polynucleotide can be observed, heated and extracted all over the areas in the circumferential direction in the capillary.

Figure 27:
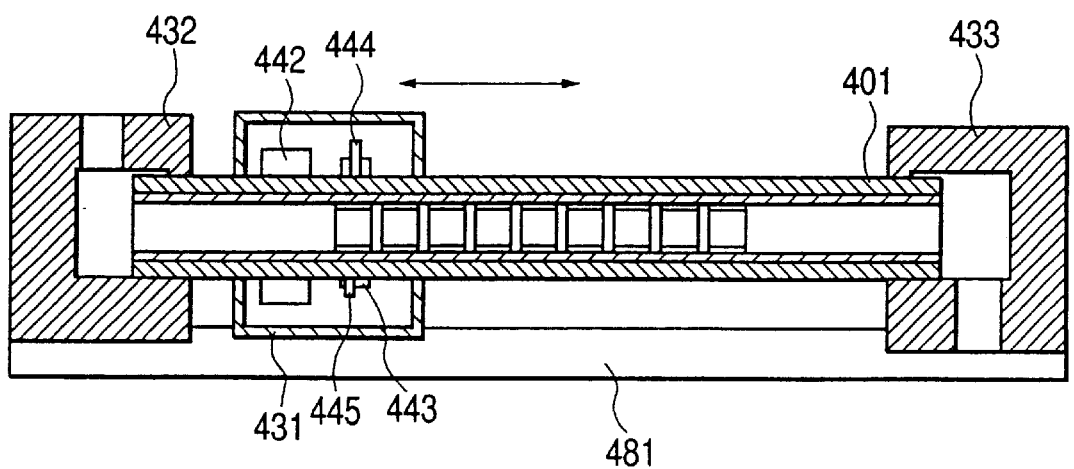
FIG. 27 is a diagram illustrating a variation of the polynucleotide separation module 431 according to the embodiment shown in FIG. 26.

FIG. 27 illustrates a variation of the polynucleotide separation module 431 according to the embodiment shown in FIG. 26. The present variation is similar to the embodiment in FIG. 26 in that an optical system is provided in the exterior of the capillary 401 but different in that only one set of the optical system identical with those to be provided in individual target polynucleotide hybridization areas in the capillary is provided in the exterior of the capillary to thereby constitute module 431, and that the module 431 is designed to be moved on rail 481 with respect to the capillary 401. By configuring like this, the apparatus can globally be miniaturized.

EMBODIMENT V

The aforementioned EMBODIMENTS I through IV are applied to the case where a target polynucleotide is contained in a sample solution, whereas EMBODIMENT V is directed to fractionate a target polynucleotide directly from cells themselves. According to the present embodiment, naturally, the target polynucleotide is finally fractionated in the form of a sample solution containing the same. Such a sample solution is, however, obtained after introducing cells to a target polynucleotide hybridization area so that the amount of target polynucleotide in the sample solution can be increased, and hence PCR or other pretreatment can be omitted in many cases. In addition, nucleotides, proteins and other cell components can be obtained for each of the cells according to the present embodiment.

Figure 28:
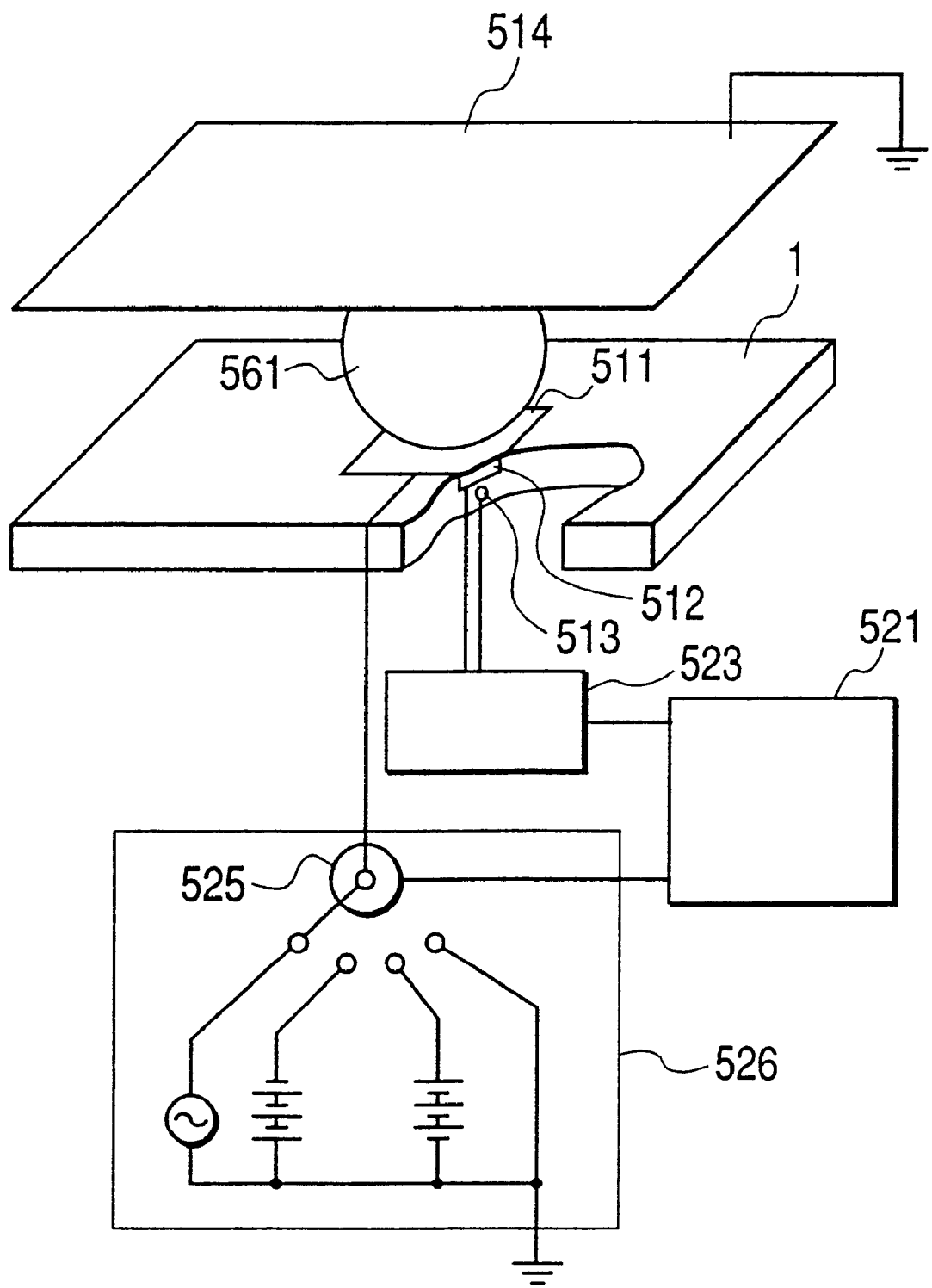
FIG. 28 is a diagram illustrating basic elements of a fifth embodiment of the invention.

FIG. 28 illustrates basic elements of the present embodiment.

On the surface of substrate 1 is formed target polynucleotide hybridization area 511 as in described in the above EMBODIMENTS. Controller 521 is to apply a DC or alternating field between an electrode of the hybridization area 511 and grounding electrode 514 opposed to the substrate 1 to capture and hybridize cell 561 in the hybridization area 511. Power supply 526 is for applying a DC or alternating field or grounding, including selection switch 525. Peltier devices 512 and temperature sensors 513 are embedded in the substrate 1 separately in the vicinity of individual target polynucleotide hybridization areas. Temperature measurement and control unit 523 is to input a signal from the temperature sensor 513 and to control the surface temperatures of the individual target polynucleotide hybridization areas independently through Peltier devices 512. Controller 521 gives a direction on which area is to be controlled in temperature.

Figure 29:
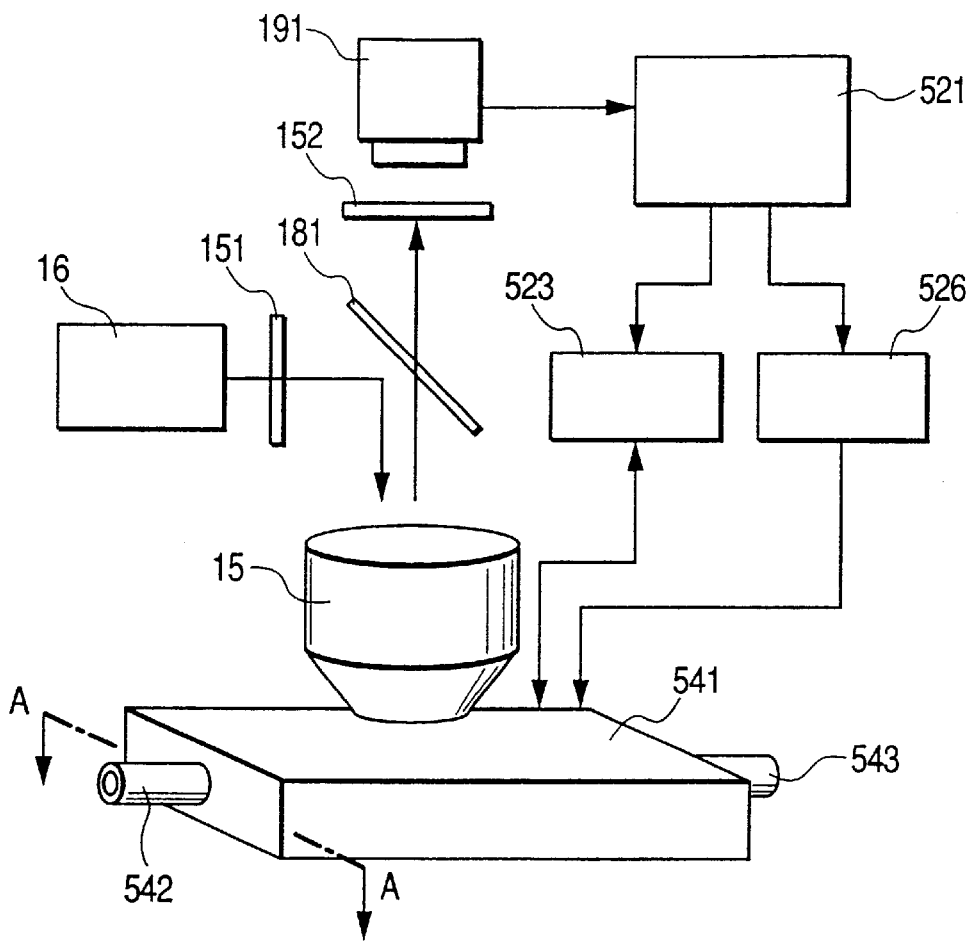
FIG. 29 is a diagram illustrating a basic configuration of the fifth embodiment including a combination of a polynucleotide separation cell having the basic elements illustrated in FIG. 28 and an optical system.
Figure 30:
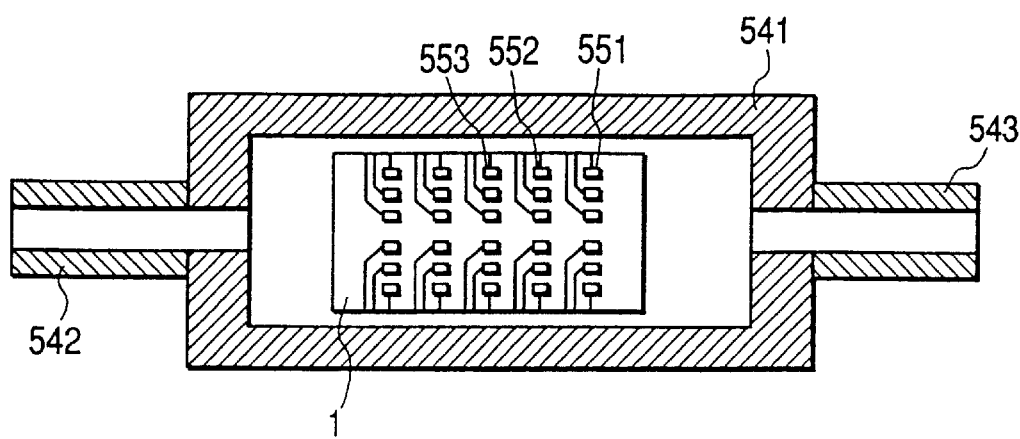
FIG. 30 is a sectional view along with the lines A—A of the separation cell illustrated in FIG. 29.

FIG. 29 illustrates a basic configuration according to the present embodiment of a combination of a polynucleotide separation cell having the basic elements illustrated in FIG. 28 and an optical system. FIG. 30 is a sectional view along with the lines A—A of the separation cell illustrated in FIG. 29.

Polynucleotide separation cell 541 is provided with sample inlet tube 542 and sample outlet tube 543, through which sample cells, washing solutions or the like are introduced into the separation cell, and cell residues, proteins, purified nucleotide samples or the like are recovered from the separation cell. In the inside of the separation cell 541 are formed, as shown in FIG. 30, target polynucleotide hybridization areas and are placed electrodes 551, 552, 553 . . . for introducing a sample cell introduced from the sample inlet tube 542 to the target polynucleotide hybridization areas, and lines are connected to the electrodes. In this figure, upper electrode 514 is not illustrated. A single stranded-oligonucleotide probe complementary to each target polynucleotide is individually immobilized in each target polynucleotide hybridization area.

The inside of the polynucleotide separation cell 541 can be observed through the same optical system as described in FIG. 2. To be more specific, the substrate 1 is placed in the direction perpendicular to the light axis of the objective lens 15, and an exciting light from light source 16 for fluorescent observation is induced via the bandpass filter 151 and the dichroic mirror 181 to the objective lens 15. The exciting light induced through the objective lens 15 excites a fluorescent dye, which is attached accompanied with a target polynucleotide hybridized onto the substrate 1, and the excited fluorescent dye emits fluorescence in an intensity in proportion to the amount of the target polynucleotide hybridized to probes on each area of the substrate. The emitted fluorescence in an intensity in proportion to the amount of the target polynucleotide is collected through the objective lens 15. Of the collected fluorescence, only a fluorescence having the wavelength to be detected is introduced via the emission filter 152 to the detector 191 to allow the observation of the inside of the separation cell 541.

In general, part of cell membrane of a cell is destroyed to liberate nucleotides, proteins and other components by heating. Consequently, by introducing a sample solution containing cells into the polynucleotide separation cell 541 and thereafter increasing the temperature of a specific target polynucleotide hybridization area on the substrate 1 up to 95° C., a cell in the area is destroyed to liberate its components, and double stranded-polynucleotides can be denatured into single stranded-polynucleotides. Subsequently, by decreasing the temperature of the hybridization area to 37° C., a single stranded-polynucleotide complementary to the probe in the area can be hybridized to the probe, among these target polynucleotides. The temperature of a specific hybridization area can be controlled by selecting a Peltier device 512 corresponding to the area and passing an electric current therethrough.

A process will be described for fractionating a cell component and target polynucleotide directly from blood cells according to the present embodiment, with reference to FIGS. 31A through 31E and FIGS. 32A through 32D.

Figure 31A:
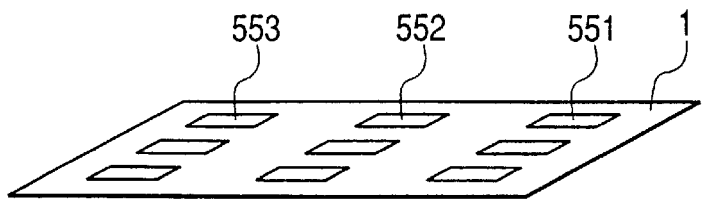
FIG. 31A is a diagram illustrating the state where target polynucleotide hybridization areas are formed on the surface of the substrate illustrated in FIG. 28.
Figure 31B:
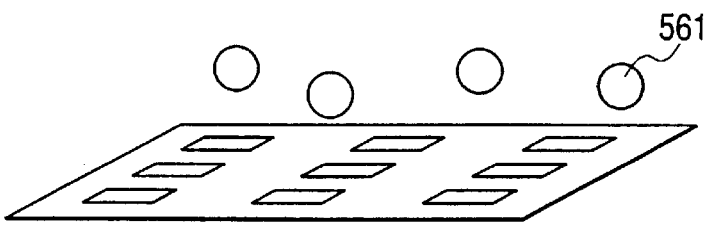
FIG. 31B is a diagram illustrating the state where a blood sample is introduced into the polynucleotide separation cell and white blood cells float over the surface of the substrate.
Figure 31C:
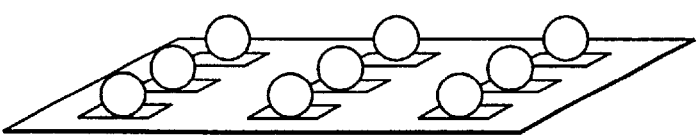
FIG. 31C is a diagram illustrating the state where white blood cells are attracted to the target polynucleotide hybridization areas by an alternating field and placed separately on each of areas.
Figure 31D:
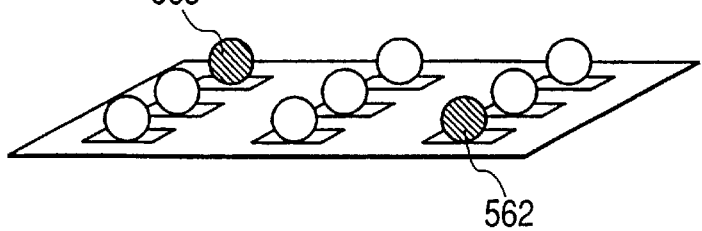
FIG. 31D is a diagram illustrating the state where white blood cells capable of making antibody response to antigen substances alone are labeled and become to emit fluorescence.
Figure 31E:
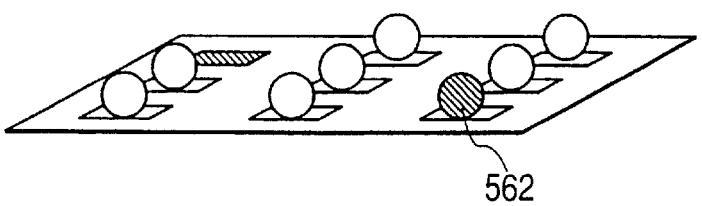
FIG. 31E is a diagram illustrating the state where only one white blood cell of those hybridized on the individual target polynucleotide hybridization areas is destroyed and disappears from the substrate.

Initially, the ion strength of a blood sample is decreased to destroy red blood cells, and thus a blood sample containing white blood cells alone as cell components is prepared. FIG. 31A illustrates the state where the target polynucleotide hybridization areas 551, 552, 553 . . . are formed on the surface of the substrate 1. FIG. 31B illustrates the state where the blood sample is introduced into the polynucleotide separation cell 541 and white blood cells 561 float over the surface of the substrate 1. In this state, an alternating field is applied between the electrodes of the target polynucleotide hybridization areas 551, 552, 553 . . . and the electrode 514 so as to attract the white blood cells 561 to the target polynucleotide hybridization areas. The gradient of electric field density generated between the electrode 514 and the electrodes of individual hybridization areas is condensed at the individual areas. An alternating field having a frequency of equal to or more than 1 kHz and a density of equal to or more than 10 V/mm can preferably used in this process. FIG. 31C illustrates the state where white blood cells are induced to, and placed on the target polynucleotide hybridization areas. In this state, a fluorescence-labeled antigen substance is introduced into the cell 541. FIG. 31D illustrates the state where only white blood cells capable of making antibody response to the antigen substance (white blood cells 562 and 563 hatched in the figure) are labeled and become to emit fluorescence. It is preferable in this state to cool the surface of the substrate to a temperature of about 4° C. and to ensure the amounts of mRNA and the like in the cells not to change accompanied with the hybridization with the marker antigen. The hybridization capability of the antibodies on the surface of B cells or the like does not change with a decreasing temperature. The position of a target polynucleotide hybridization area where a white blood cell emitting fluorescence can, therefore, be identified through the output of the detector 191. The component of a cell having reactivity with the antigen substance can be liberated into the sample solution by heating individual target polynucleotide hybridization areas in sequence to destroy the cells. FIG. 31E illustrates the state where only one white blood cell 563 of those hybridized on the individual target polynucleotide hybridization areas is destroyed and disappears from the substrate 1. Accordingly, the component of the specific white blood cell can be extracted by recovering the sample solution in the polynucleotide separation cell 541 while applying an alternating field to other cells in this state.

Figure 32A:
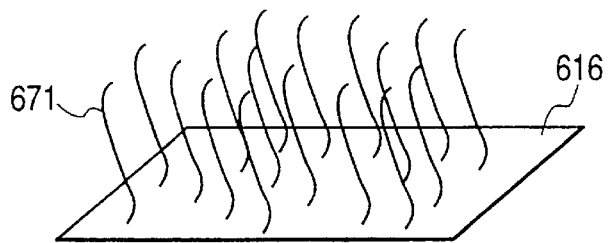
FIG. 32A is a diagram illustrating the state where probes are immobilized on one target polynucleotide hybridization area.
Figure 32B:
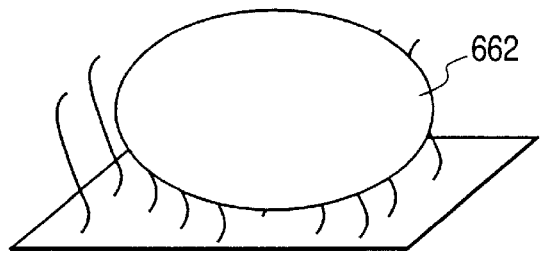
FIG. 32B is a diagram illustrating the state where a white blood cell is inducted and hybridized to the target polynucleotide hybridization area.
Figure 32C:
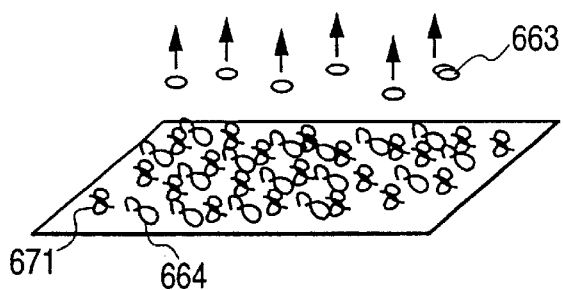
FIG. 32C is a diagram schematically illustrating the state where polynucleotides and proteins migrate by electrophoresis respectively in the opposite direction to each other.

FIG. 32A illustrates the state where probes 671 are immobilized on one area 616 of the target polynucleotide hybridization areas. FIG. 32B illustrates the state where white blood cell 662 is induced and hybridized to the hybridization area 616 in the above manner. After the white blood cell 662 is induced to the hybridization area 616 as thus, the sample solution is exchanged with a new one to decrease its pH to about 4. This is because almost all of pK values of proteins range 4 or higher and by decreasing pH to 4 or lower, total charges of proteins become positive whereas the charges of polynucleotides become negative; and hence the both can be separated in a DC field. Under such a pH condition, the temperature of the hybridization area 616 is increased by the Peltier device 512 to destroy the white blood cell. Thereafter, by setting the electrode in the target polynucleotide hybridization area 616 as an anode and the electrode 514 on the opposite surface as a cathode, polynucleotides 664 are collected to the hybridization area 616 and proteins 663 are electrophoresed to the face of the counter electrode 514. FIG. 32C is a schematic diagram illustrating the state where polynucleotides 664 and proteins 663 migrate by electrophoresis in the opposite direction to each other. The proteins can easily be separated from polynucleotides by replacing the solution in the cell. In this process, polynucleotides complementary to the probe 671 immobilized on the hybridization area naturally hybridize to the probes.

Figure 32D:
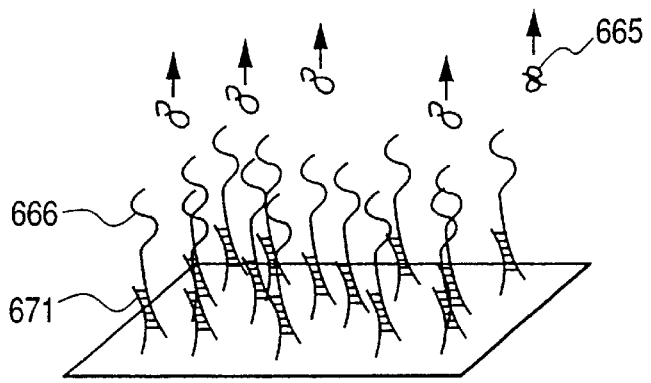
FIG. 32D is a diagram schematically illustrating the state where polynucleotide not hybridized to probes of the target polynucleotide hybridization area migrate by electrophoresis.

Next, by setting the electrode of the hybridization area as a cathode and the counter electrode 514 as an anode, the target polynucleotide 666 hybridized to the probes 671 on the hybridization area 616 remains on the area 616, while polynucleotides not hybridized are liberated into the sample solution. Of polynucleotides in the white blood cell 662, those not hybridized to the probes 671 can be extracted as in a sample solution by recovering the sample solution in the present step. FIG. 32D schematically illustrates the state where polynucleotides 665 not hybridized to probes 671 migrate by electrophoresis.

Finally, a specific target polynucleotide hybridized to the probes in a specific target polynucleotide hybridization area is liberated by increasing the temperature of the specific area up to about 95° C. By recovering the sample solution in this step, the objected target polynucleotide such as mRNA can be extracted and recovered.

After completion of the aforementioned procedure for on white blood cell, a next white cell is subjected to the same procedure to extract a mRNA or other target polynucleotide per each white blood cell. Separately, the extraction can be conducted by dying cells with different plural types of markers by a marker labeling technique and observing them with different filters to select and extract a cell meeting a plurality of conditions.

The total amount of the target polynucleotide can quantitatively determined through signals from the optical system in the state where the target polynucleotide is hybridized to the probes in the target polynucleotide hybridization area. Consequently, the present embodiment can be applied to the determination of the total amount of mRNA in a B cell or other white blood cell, and according to the embodiment, a condition can be clarified easily and rapidly by estimating the activity of a white blood cell having reactivity to a specific antigen.

The present embodiment can naturally be applied to arbitrary cells in addition to white blood cells.

Other embodiments and variations will be obvious to those skilled in this art, this invention is not to be limited except as set forth in the following claims.

What is claimed is:

1. A cell components recovering method comprising the steps of:
   (1) supplying a sample solution containing cells on a surface of a substrate in a separation cell, and capturing each of said cells one by one separately on each of a plurality of independent areas formed on the surface of the substrate;
   (2) binding a fluorescence-labeled substance to said cells to thereby selectively label cells by a binding reaction;
   (3) identifying the positions of said areas where said cells labeled with the fluorescence labeled substance emit fluorescence upon irradiation with an excitation light;
   (4) heating the surface of the substrate at one of the identified positions in step (3) to a predetermined temperature to destroy said cell captured at the one of the identified positions, to liberate cell components from said cell captured at the one of the identified positions into said separation cell;
   (5) recovering said liberated cell components from said separation cell by introducing a washing solution into said separation cell, whereby said cells at the areas, except for said area at the one of the identified positions, remain on the areas, respectively, and recovering said wash solution to thereby recover said liberated cell components; and
   (6) repeating the steps (4) and (5), by changing a position of the identified positions in step (3).

2. A cell components recovering method according to claim 1, wherein said cell is a white blood cell.

3. A cell components recovering method comprising the steps of:
   (1) supplying a sample solution containing cells on a surface of a substrate in a separation cell, and capturing each of said cells one by one separately on each of a plurality of independent areas formed on the surface of the substrate;
   (2) binding a fluorescence-labeled substance to said cells to thereby selectively label cells by a binding reaction;
   (3) identifying the positions of said areas where said cells labeled with the fluorescence-labeled substance emit fluorescence upon irradiation with an excitation light;
   (4) destroying said cell captured at the one of the identified positions in step (3), to liberate cell components from said cell captured at one of the identified positions into said separation cell;
   (5) recovering said liberated cell components from said separation cell by introducing a washing solution into said separation cell, whereby said cells at the areas, except for said area at the one of the identified positions, remain on the areas, respectively, and recovering said wash solution to thereby recover said liberated cell components; and
   (6) repeating the steps (4) and (5), by changing a position of the identified positions in step (3).

4. A cell components recovering method according to claim 3, wherein said cell is a white blood cell.

5. A cell components recovering method comprising the steps of:
   (1) supplying a sample solution containing cells on a surface of a substrate in a separation cell, and capturing each of said cells one by one separately on each of a plurality of independent areas formed on the surface of the substrate;
   (2) introducing a fluorescence-labeled antigen substance into said separation cell to thereby label cells which make an antibody response to the antigen substance;

(3) identifying the positions of said areas where said cells labeled with the fluorescence-labeled antigen substance emit fluorescence upon irradiation with an excitation light;

(4) heating the surface of the substrate at one of the identified positions in step (3) to a predetermined temperature to destroy said cell captured at the one of the identified positions, to liberate cell components from said cell, having antibody response to the antigen substance and being captured at the one of the identified positions, into said separation cell;

(5) recovering said liberated cell components from said separation cell by introducing a washing solution into said separation cell, whereby said cells at the areas, except for said area at the one of the identified positions, remain on the areas, respectively, and recovering said wash solution to thereby recover said liberated cell components; and (6) repeating steps (4) and (5), by changing a position of the identified positions in the step (3).

6. A cell components recovering method according to claim 5, wherein said cell is a white blood cell.

7. A cell components recovering method comprising the steps of:

(1) supplying a sample solution containing cells on a surface of a substrate in a separation cell, and capturing each of said cells one by one separately on each of a plurality of independent areas formed on the surface of the substrate;

(2) introducing a fluorescence-labeled antigen substance into said separation cell to thereby label cells which make an antibody response to the antigen substance;

(3) identifying the positions of said areas where said cells labeled with the fluorescence-labeled antigen substance emit fluorescence upon irradiation with an excitation light;

(4) destroying said cell captured at the one of the identified positions in step (3), to liberate cell components from said cell having antibody response to the antigen substance and being captured at one of the identified positions into said separation cell;

(5) recovering said liberated cell components from said separation cell by introducing a washing solution into said separation cell, whereby said cells at the areas, except for said area at the one of the identified positions, remain on the areas, respectively, and recovering said wash solution to thereby recover said liberated cell components; and (6) repeating steps (4) and (5), by changing a position of the identified positions in the step (3).

8. A cell components recovering method according to claim 7, wherein said cell is a white blood cell.

9. A cell components recovering method comprising the steps of:

(1) preparing a sample solution containing white blood cells from a blood sample;

(2) supplying said sample solution on a surface of a substrate in a separation cell;

(3) capturing each of said white blood cells one by one separately on each of a plurality of independent areas formed on the surface of the substrate, by applying an alternating field between electrodes of said areas and an electrode opposed to the substrate;

(4) introducing a fluorescence-labeled antigen substance into said separation cell, labeling to thereby label said white blood cells which make an antibody response to the antigen substance;

(5) identifying the positions of said areas where said white blood cells labeled with the fluorescence-labeled antigen substance emit fluorescence upon irradiation with an excitation light;

(6) heating the surface of the substrate at one of the identified positions in step (5) to a predetermined temperature to destroy said white blood cell captured at the one of the identified positions, to liberate cell components from said white blood cell having antibody response to the antigen substance and being captured at the one of the identified positions into said separation cell;

(7) recovering said liberated cell components from said separation cell by introducing a washing solution into said separation cell, whereby said white blood cell at the areas, except for said area at the one of the identified positions, remain on the areas, respectively, and recovering said wash solution to thereby recover said liberated cell components, by applying the alternating field between the electrode opposed to the substrate and the electrodes of the areas except for said area at the one of the identified positions; and (8) repeating steps (6) and (7), by changing a position of the identified positions in step (5).

* * * * *